United States Patent
He et al.

(10) Patent No.: US 8,575,354 B1
(45) Date of Patent: Nov. 5, 2013

(54) FUSED THIOPHENES AND METHODS FOR MAKING AND USING SAME
(71) Applicant: Corning Incorporated, Corning, NY (US)
(72) Inventors: Mingqian He, Horseheads, NY (US); Thomas Mark Leslie, Horseheads, NY (US); Feixia Zhang, Shanghai (CN)
(73) Assignee: Corning Incorporated, Corning, NY (US)
( * ) Notice: Subject to any disclaimer, the term of this patent is extended or adjusted under 35 U.S.C. 154(b) by 0 days.
(21) Appl. No.: 13/920,502
(22) Filed: Jun. 18, 2013

Related U.S. Application Data

(62) Division of application No. 12/935,426, filed as application No. PCT/US2009/001965 on Mar. 30, 2009, now Pat. No. 8,487,114.
(60) Provisional application No. 61/072,468, filed on Mar. 31, 2008.

(51) Int. Cl.
*C07D 263/08* (2006.01)
*C07D 495/22* (2006.01)
(52) U.S. Cl.
USPC ............................................. 548/105; 549/3
(58) Field of Classification Search
USPC ............................................. 548/105; 549/3
See application file for complete search history.

(56) References Cited

U.S. PATENT DOCUMENTS

2007/0265418 A1  11/2007  He et al. .................. 528/226

FOREIGN PATENT DOCUMENTS

CN    101111497        1/2008
JP    62-039592    *   2/1987 ............... C07F 7/22

OTHER PUBLICATIONS

Mazaki, Yasuhiro et al., Synthesis of tetrathieno-acene and pentathieno-acene: UV-spectral trend in a homologous series of thieno-acenes, Tetrahedron Letters (1989), 30(25), 3315-18.

Zhang, X. et al., Synthesis and Structure of Fused α-Oligothiophenes with up to Seven Rings, J. Am. Chem. Soc., 2005, 127, 10502.
McCulloch, I. et al., Liquid-crystalline semiconducting polymers with high charge-carrier mobility, Nat. Mater., 2006, 5, 328.
Yanming Sun et al., Organic thin-film transistors with high mobilities and low operating voltages based on 5,5'-bis-biphenyl-dithieno[3,2-b:2',3'-d]thiophene semiconductor and polymer gate dielectric, Applied Physics Letters, 88, 242113, 2006.
Fabio Cicoira et al., Organic Light Emitting Transistors Based on Solution-Cast and Vacuum-Sublimed Films of a Rigid Core Thiophene Oligomer, Advanced Material 2006,18,169-174.
He, M. et al., Synthesis and Structure of Alkyl-Substituted Fused Thiophenes Containing up to Seven Rings, Org. Chem., 2007, 72, 442.
Yamagishi, M. et al., High-mobility double-gate organic single-crystal transistors with organic crystal gate insulators, Appl. Phys. Lett, 2007, 90, 182117.

* cited by examiner

*Primary Examiner* — Joseph Kosack
(74) *Attorney, Agent, or Firm* — Jason A. Barron

(57) ABSTRACT

Disclosed are compounds having one of the following formulae:

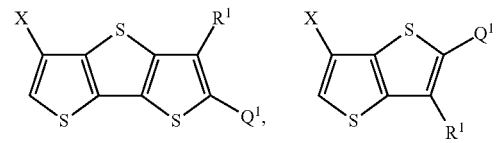

wherein X is an aromatic nucleophilic substitution leaving group; $R^1$ is hydrogen, an alkyl group, or an aryl group; and $Q^1$ is a carboxyl protecting group or an aldehyde protecting group. Also disclosed are fused thiophenes that can be prepared using these compounds, as well as stannylthio-containing thiophene, thienothiophene, and dithienothiophene compounds that can be used to prepare fused thiophenes. Methods for making and using the aforementioned compounds, fused thiophenes, and stannylthio-containing thiophene, thienothiophene, and dithienothiophene compounds are also disclosed.

10 Claims, 8 Drawing Sheets

FUSED THIOPHENES AND METHODS FOR MAKING AND USING SAME

CROSS-REFERENCE TO RELATED APPLICATIONS

This application is a Divisional Application of and claims the benefit of priority to U.S. Non-Provisional patent application Ser. No. 12/935,426, filed on Sep. 29, 2010, which is a 371 of and claims the benefit of priority to International Patent Application No. PCT/US09/01965, filed on Mar. 30, 2009, which is a Non-Provisional Patent Application of and claims the benefit of priority to U.S. Provisional Patent Application No. 61/072,468, filed on Mar. 31, 2008, the contents of which are relied upon and incorporated herein by reference in their entirety.

TECHNICAL FIELD

The present invention relates, generally, to heterocyclic organic compounds and, more particularly, to fused thiophene compounds and to methods for making and using same.

BACKGROUND

Highly conjugated organic materials are currently the focus of great research activity, chiefly due to their interesting electronic and optoelectronic properties. They are being investigated for use in a variety of applications, including field effect transistors (FETs), thin-film transistors (TFTs), organic light-emitting diodes (OLEDs), electro-optic (EO) applications, as conductive materials, as two photon mixing materials, as organic semiconductors, and as non-linear optical (NLO) materials. Highly conjugated organic materials may find utility in devices such as radio frequency identification (RFID) tags, electroluminescent devices in flat panel displays, and in photovoltaic and sensor devices.

Materials such as pentacene, poly(thiophene), poly(thiophene-co-vinylene), poly(p-phenylene-co-vinylene) and oligo(3-hexylthiophene) have been intensively studied for use in various electronic and optoelectronic applications. More recently, fused thiophene compounds have been found to have advantageous properties. For example, bisdithieno[3,2-b:2',3'-d]thiophene (1, j=2) has been found to efficiently π-stack in the solid state, to have a high mobility (up to 0.05 cm²/V·s), and to have a high on/off ratio (up to $10^8$). Oligomers and polymers of fused thiophenes, such as oligo- or poly(thieno[3,2-b]thiophene) (2) and oligo- or poly(dithieno[3,2-b:2'-3'-d]thiophene) (1)

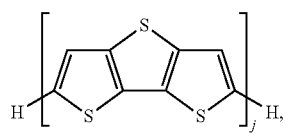

(1)

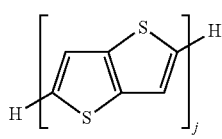

(2)

have also been suggested for use in electronic and optoelectronic devices and have been shown to have acceptable conductivities and non-linear optical properties.

We have described some fused thiophene-based materials in U.S. Patent Application No. US2007/0161776 of He and in PCT Patent Application Publication No. WO 2006/031893 of He. A need for new fused thiophenes and methods for making fused thiophenes continues to exist, and the present invention is directed, in part, to addressing this need.

SUMMARY

The present invention relates to a compound having one of the following formulae 11 or 12:

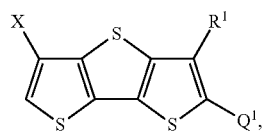

11

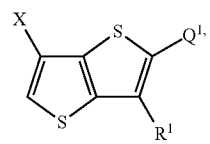

12 wherein X is an aromatic nucleophilic substitution leaving group; $R^1$ is hydrogen, an alkyl group, or an aryl group; and $Q^1$ is a carboxyl protecting group or an aldehyde protecting group.

The present invention also relates to a compound having one of the following formulae 14, 15, 16, or 17:

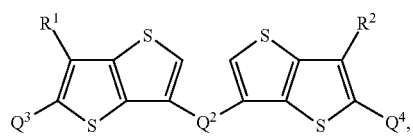

14

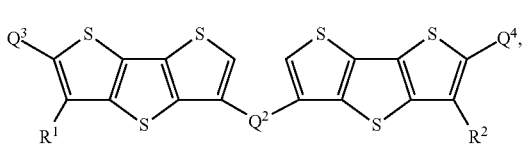

15

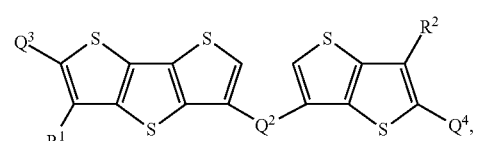

16

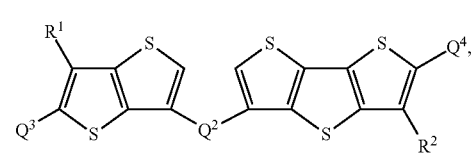

17 wherein $R^1$ and $R^2$ are the same or different and are selected from hydrogen, alkyl, and aryl; $Q^3$ and $Q^4$ are independently selected from hydrogen, a carboxylic acid, a carboxylic acid derivative, an alkyl group, an aryl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, or a halide; and $Q^2$ has one of the following formulae 18, 19, 20, 21A, or 21B:

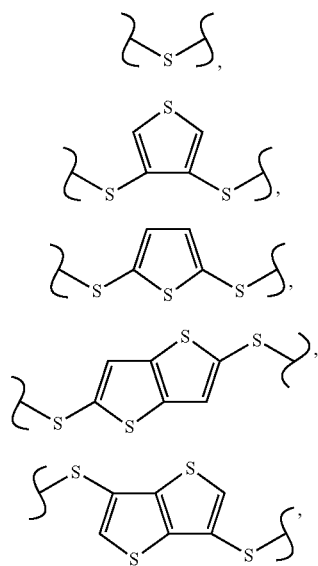

or one of the following formulae 22A, 22B, 22C, 22D, or 22E:

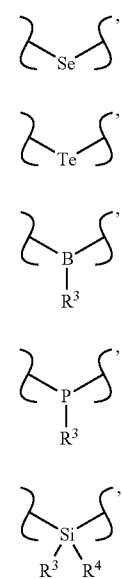

wherein $R^3$ and $R^4$ are the same or different and are selected from alkyl and aryl.

The present invention also relates to a compound having the following formula 23:

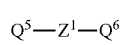

wherein $Z^1$ has one of the following formulae wherein $Z^1$ has one of the following formulae 24A, 24B, 24C, 24D, 25, 26, 27, 28, 29, or 30:

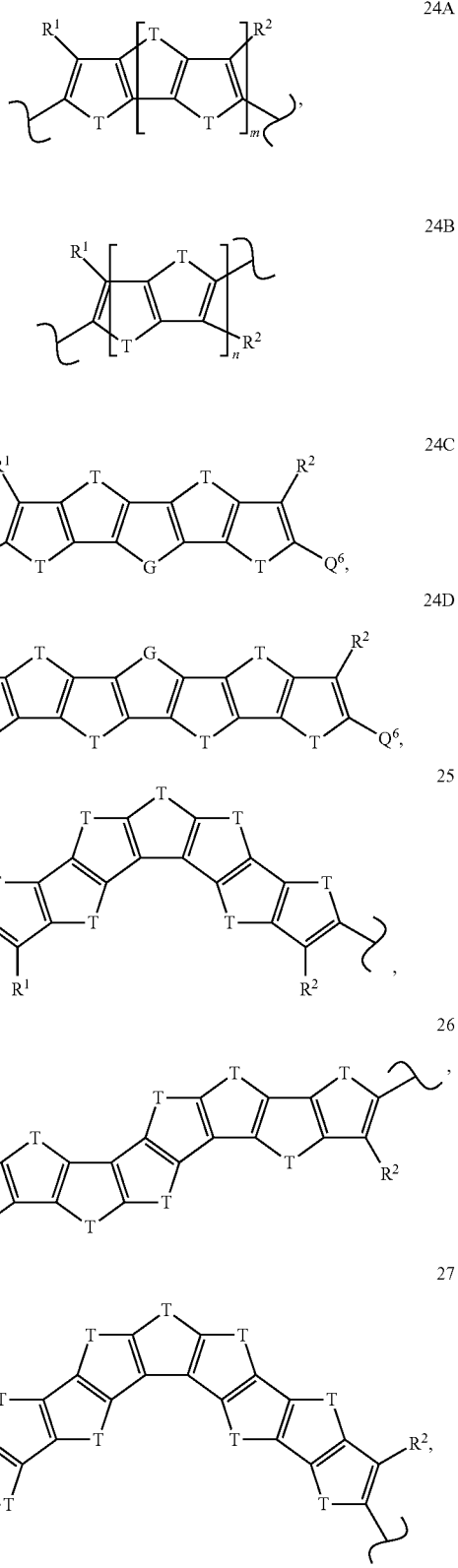

-continued

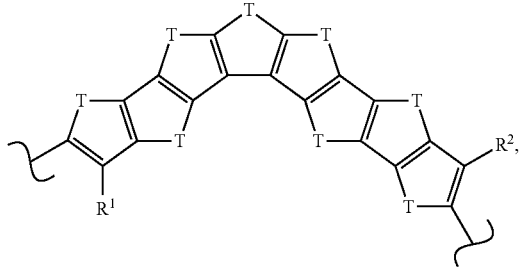
28

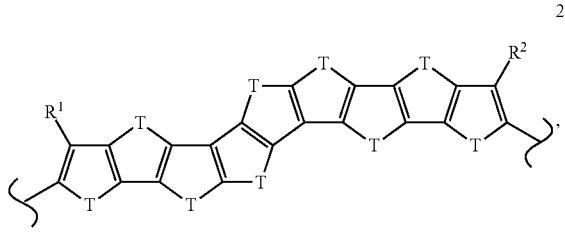
29

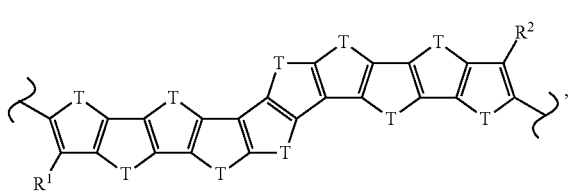
30 wherein n is 3, 4, or 5; m is 2, 3, or 4; G is selected from —Se—, —Te—, —B(R³)—, —P(R³)—, and —Si(R³)(R⁴)—; each T is independently selected from S and SO₂; $R^1$ and $R^2$ are the same or different and are selected from hydrogen, alkyl, and aryl; $Q^5$ and $Q^6$ are the same or different and are selected from hydrogen, a carboxylic acid, a carboxylic acid derivative, an alkyl group, an aryl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, or a halide, provided that, when $Z^1$ has formula 24A or 24B, at least one of $Q^5$ and $Q^6$ is a thioester, an oxazoline moiety, or an acetal.

The present invention also relates to a compound having one of the following formulae 37, 38, 39, or 40:

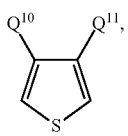
37

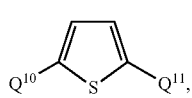
38

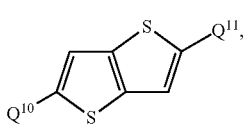
39

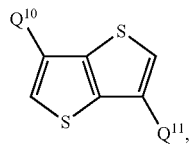
40 wherein $Q^{10}$ and $Q^{11}$ are the same or different and have the formula:

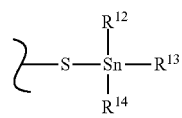

wherein $R^{12}$, $R^{13}$, and $R^{14}$ are independently selected from alkyl and aryl.

The present invention also relates to a compound having one of the following formulae 41, 42, 43, 44, 45, or 46.

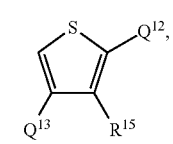
41

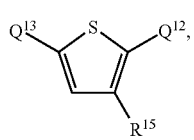
42

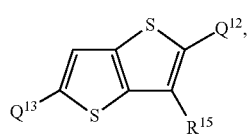
43

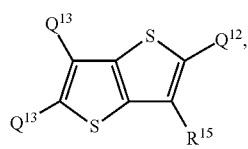
44

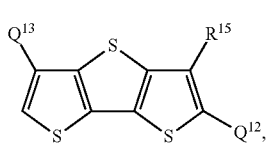
45

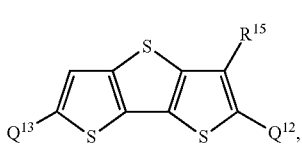
46 wherein $R^{15}$ is selected from hydrogen, alkyl, and aryl; wherein $Q^{12}$ is selected from hydrogen, a carboxylic acid, a carboxylic acid derivative, an alkyl group, an aryl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, or a halide; and wherein $Q^{13}$ has the formula:

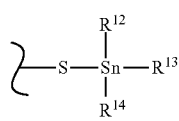

wherein $R^{12}$, $R^{13}$, and $R^{14}$ are independently selected from alkyl and aryl.

These and additional features and embodiments of the present invention will be more fully illustrated and discussed in the following drawings and detailed description.

Figure 1A:
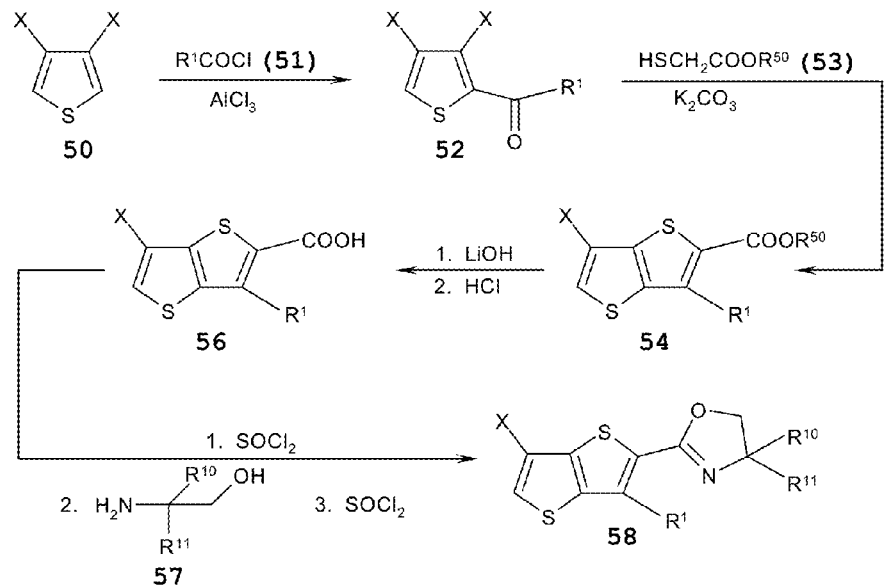
FIGS. 1A and 1B are synthetic schemes that can be used to prepare certain compounds of the present invention.

The embodiments set forth in the figures are illustrative in nature and not intended to be limiting of the invention defined by the claims. Individual features of the drawings and the invention will be more fully discussed in the following detailed description.

DETAILED DESCRIPTION

Before the present materials, articles, and/or methods are disclosed and described, it is to be understood that the aspects described below are not limited to specific compounds, synthetic methods, or uses, but is to be understood to be illustrative of the invention. It is also to be understood that the terminology used herein is for the purpose of describing particular aspects only and is not intended to be limiting.

In this specification and in the claims that follow, reference will be made to a number of terms that shall be defined to have the following meanings:

Throughout this specification and claims, unless the context requires otherwise, the word "comprise" or variations, such as "comprises" or "comprising", will be understood to imply the inclusion of a stated element, integer, or step or group of elements, integers, or steps but not the exclusion of any other element, integer, or step or group of elements, integers, or steps.

It must be noted that, as used in the specification and the appended claims, the singular forms "a", "an", and "the" include plural referents unless the context clearly dictates otherwise. Thus, for example, reference to "a compound" is meant to include mixtures of two or more such compounds; reference to "a moiety" is meant to include mixtures of two or more such moieties; and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about", it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

The term "alkyl group" as used herein is a saturated hydrocarbon group of 1 to 40 carbon atoms. As used herein, "alkyl" is meant to include linear alkyls, branched alkyls, and cycloalkyls, each of which can be substituted or unsubstituted. "Alkyl" is also meant to include lower linear alkyls (e.g., C1-C6 linear alkyls), such as methyl, ethyl, n-propyl, n-butyl, n-pentyl, and n-hexyl; lower branched alkyls (e.g., C3-C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-1-ethylpropyl, and the like; and lower cycloalkyls (e.g., C3-C8 cycloalkyls), such as cyclopropyl, cyclobutyl, cyclopentyl, cyclohexyl, and the like. "Alkyl", as use herein, is meant to include unsubstituted alkyls, such as those set forth above, in which no atoms other than carbon and hydrogen are present. "Alkyl", as use herein, is also meant to include substituted alkyls. Suitable substituents include aryl groups (which may themselves be substituted), heterocyclic rings (saturated or unsaturated and optionally substituted), alkoxy groups (which is meant to include aryloxy groups (e.g., phenoxy groups)), amine groups (e.g., disubstituted with aryl or alkyl groups), carboxylic acid derivatives (e.g., carboxylic acid esters, amides, etc.), halogen atoms (e.g., Cl, Br, and I), and the like. Further, alkyl groups bearing one or more alkenyl or alkynyl substituents (e.g., a methyl group itself substituted with a prop-1-en-1-yl group to produce a but-2-en-1-yl substituent) is meant to be included in the meaning of "alkyl". Other suitable substituents include hydroxy groups and protected hydroxy groups (e.g., an acyloxy group, such at an acetoxy group; a silyl ether group, such as a trimethylsilyl (TMS) ether group and a tert-butyldimethylsilyl (TBS) ether group; and the like). As noted above, the alkyl group can be substituted or unsubstituted. The term "unsubstituted alkyl group" is defined herein as an alkyl group composed of just carbon and hydrogen. The term "substituted alkyl group" is defined herein as an alkyl group with one or more hydrogen atoms substituted with a group including, but not limited to, an aryl group, cycloalkyl group, aralkyl group, an alkenyl group, an alkynyl group, an amino group (e.g., an unsubstituted amino group, a monosubstituted amino group, or a disubstituted amino group), a carboxylic acid, an amide, an ester, an aldehyde, a hydroxyl group, an alkoxy group, a thiol group (which may be unsubstituted or substituted with, for example, and alkyl or aryl group), a halide, an acyl halide, an acrylate, or a vinyl ether. As also noted above, the term "alkyl group" as used herein also includes cycloalkyl groups. The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term cycloalkyl group also includes a heterocycloalkyl group, where at least one of the carbon atoms of the ring is replaced with a heteroatom such as, but not limited to, nitrogen, oxygen, sulfur, or phosphorus. As indicated above, the term "alkyl group" as used herein also includes aralkyl groups. The term "aralkyl" as used herein is an alkyl group having an aryl group (as defined herein) attached to the alkyl group. An example of an aralkyl group is a benzyl group.

As used herein, "alkoxy" is meant to include groups having the formula —O—R, where R is an alkyl or aryl group. They include methoxy, ethoxy, propoxy, phenoxy, 4-methylphenoxy, and the like.

As used herein, "aryl" is meant to include aromatic rings, for example, aromatic rings having from 4 to 12 members, such as phenyl rings. These aromatic rings can optionally contain one or more heteroatoms (e.g., one or more of N, O, S, and P), and, thus, "aryl", as used herein, is meant to include heteroaryl moieties, such as thienyl rings, pyridyl rings, and furanyl rings. The aromatic rings can be optionally substituted. "Aryl" is also meant to include aromatic rings to which are fused one or more other aryl rings or non-aryl rings. For example, naphthyl groups, indole groups, thienothienyl groups, dithienothienyl, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), hydroxy groups, aldehyde groups, nitro groups, amine groups (e.g., unsubstituted, or mono- or di-substituted with aryl or alkyl groups), carboxylic acid groups, carboxylic acid derivatives (e.g., carboxylic acid esters, amides, etc.), halogen atoms (e.g., Cl, Br, and I), and the like.

As used herein, "ring" refers to a homocyclic or heterocyclic ring which can be saturated or unsaturated, aromatic or non-aromatic. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems. In the case where the ring is saturated (i.e., in the case where each of the atoms making up the ring are joined by single bonds to other members of the ring), the ring may optionally include unsaturated (aromatic or nonaromatic) or saturated substituents.

The term "alkenyl group" is defined as a branched or unbranched hydrocarbon group of 2 to 40 carbon atoms containing at least one carbon-carbon double bond.

The term "alkynyl group" is defined as a branched or unbranched hydrocarbon group of 2 to 40 carbon atoms containing at least one carbon-carbon triple bond.

In the specification that follows, compounds, compositions, methods, and the like, may be disclosed as containing a combination of components. When combinations of such components are disclosed, while specific reference to each individual and collective combination, permutation, or subset of these components may not be explicitly disclosed, each individual and collective combination, permutation, and subset is specifically contemplated and is to be considered as being particularly described herein. For example, if a class of components A, B, and C are disclosed; and a class of components D, E, and F are disclosed; and an example of a combination, A-D, is disclosed, then, even if each combination is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed. By way of further illustration, this concept applies to mixtures of various compounds or other components in compositions; combinations of various components in devices; and the like.

One aspect of the present invention relates to a compound having one of the following formulae 11 or 12:

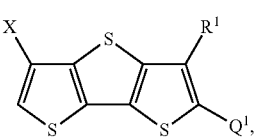

11

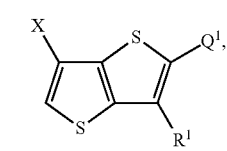

12 wherein X is an aromatic nucleophilic substitution leaving group; $R^1$ is hydrogen, an alkyl group, or an aryl group; and $Q^1$ is a carboxyl protecting group or an aldehyde protecting group.

Examples of carboxyl protecting groups include esters, thioesters, and oxazolines. Examples of aldehyde protecting groups include acetals, such as cyclic acetals. As one skilled in the art will appreciate, choice of a particular carboxyl protecting group or aldehyde protecting group will depend on the use to which compounds of formula 11 or formula 12 are to be put. For example, in those cases where compounds of formula 11 or formula 12 are to be used as starting materials in further syntheses (such as the syntheses described below), the particular carboxyl protecting group or aldehyde protecting groups would be chosen based on its stability to subsequent reaction conditions, the availability of deprotection chemistries that are compatible with other substituents that might be present, etc.

As particular examples of $Q^1$, there can be mentioned linear alkyl esters (e.g., linear C1-C8 alkyl esters, such as methyl esters, for example, where $Q^1$ is —COOCH$_3$); tertiary alkyl esters (e.g., tertiary C4-C8 alkyl esters, such as t-butyl esters, for example, where $Q^1$ is —COOC(CH$_3$)$_3$); aralkyl esters (e.g., (C6-C10)aryl-substituted-(C1-C4)alkyl esters, such as benzyl esters, for example, where $Q^1$ is —COOCH$_2$ (C$_6$H$_5$)); and tertiary alkyl thioesters (e.g., tertiary C4-C8 alkyl thioesters, such as t-butyl thioesters, for example, where $Q^1$ is —C(O)SC(CH$_3$)$_3$). As noted above, $Q^1$ can be an oxazoline moiety, such as a 1,3-oxazolin-2-yl moiety, for example, as in the case where $Q^1$ has the formula:

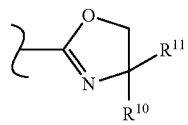

in which $R^{10}$ and $R^{11}$ are the same or different and are selected from hydrogen, alkyl (e.g., a substituted or unsubstituted C1-C8 alkyl), and aryl (e.g., a substituted or unsubstituted phenyl) or $R^{10}$ and $R^{11}$, together with the carbon atom to which they are bound, form a ring (e.g., a 4- to 8-membered (such as a 5-membered, 6-membered, etc.) homocyclic or heterocyclic ring). Illustratively, $R^{10}$ and $R^{11}$ can be the same or different lower alkyl, such as in the case where $R^{10}$ and $R^{11}$ are the same or different and are selected from a C1-C6 alkyl. In certain embodiments, $R^{10}$ and $R^{11}$ are the same lower alkyl, for example as in the case where each of $R^{10}$ and $R^{11}$ is a methyl group, an ethyl group, a n-propyl group, and i-propyl group, etc.

As noted above, X is an aromatic nucleophilic substitution leaving group. As used in this context, "aromatic nucleophilic substitution leaving group" is meant to refer to those leaving groups appropriate to aromatic nucleophilic substitution, such as those disclosed in March, *Advanced Organic Chemistry* (4th edition), Wiley Interscience, 1992, page 652, which is hereby incorporated by reference. Examples of suitable leaving groups include F, Cl, Br, I, and sulfonic esters (e.g. tosylate, mesylate, besylate, and triflate).

As noted above, $R^1$ can be a hydrogen, an alkyl group, or an aryl group. Illustratively, $R^1$ can be a variety of substituted or unsubstituted alkyl groups. For example, $R^1$ can be an unsubstituted alkyl group, such as a straight-chain alkyl group (e.g. methyl, ethyl, propyl, butyl, pentyl, hexyl, heptyl, octyl, nonyl, decyl, undecyl, dodecyl or hexadecyl), a branched alkyl group (e.g. sec-butyl, neo-pentyl, 4-methylpentyl), or a substituted or unsubstituted cycloalkyl group (e.g. cyclopentyl, cyclohexyl). In certain embodiments, $R^1$ is an alkyl group at least four carbons in size. In certain embodiments, $R^1$ is a substituted alkyl group at least four carbons in size. In certain embodiments, $R^1$ is a substituted alkyl group at least four carbons in size in which substitution of the alkyl group is separated from the fused thiophene ring system by at least two carbons. In certain embodiments, $R^1$ is a substituted alkyl group (e.g., an alkyl group substituted with an aryl group, a cycloalkyl group, an aralkyl group, an alkenyl group, an alkynyl group, an amino group, an ester, an aldehyde, a hydroxyl group, an alkoxy group, a thiol group, a thioalkyl group, a halide, an acyl halide, an acrylate, or a vinyl ether). Examples of substituted alkyl groups include, but are not limited to, 6-hydroxyhexyl and 3-phenylbutyl. The selection of $R^1$ can depend on the end use of the compound. The methods described herein permit the synthesis of fused thiophene moieties having a wide variety of $R^1$ substituents. Any functionality that might be present on a substituted alkyl or aryl $R^1$ group can be protected, for example, in order to survive subsequent reaction steps.

The aforementioned compounds having formula 11 or 12 can be prepared by any suitable method.

For example, compounds having formula 12 can be prepared following the procedures described in FIG. 1A. Referring to FIG. 1A, thiophene 50 (e.g., dibromothiophene) can be reacted with an acid chloride (e.g., acid chloride 51), for example, in the presence of a Friedel-Crafts compatible Lewis acid, such as a stoichiometric amount of AlCl$_3$, to produce ketone 52. Ketone 52 can be converted to thienothiophene ester 54, for example, by reaction with 2-mercaptoacetate 53 (e.g., in which $R^{50}$ is an alkyl or aryl group, such as an ethyl group or another unsubstituted C1-C4 alkyl group) in the presence of a base, such as potassium carbonate. Thienothiophene ester 54 can be converted to thienothiophene free acid 56, for example by hydrolyzing thienothiophene ester 54 in the presence of lithium hydroxide, followed by acidification (e.g., with hydrochloric acid). Thienothiophene free acid 56 can be converted to oxazolinyl thienothiophene 58 by converting the free acid to the corresponding acid chloride (using, for example, thionyl chloride, oxalyl chloride, etc.), followed by reaction of the acid chloride with 1-amino-2-hydroxyalkane 57 (e.g., in which $R^{10}$ and $R^{11}$ are the same or different and are selected from hydrogen, alkyl, and aryl or in $R^{10}$ and $R^{11}$, together with the carbon atom to which they are bound, form a ring, for example as described above), followed by treatment with a dehydrating agent, such as thionyl chloride, phosphorus pentoxide, oxalyl chloride, and the like.

Figure 1B:
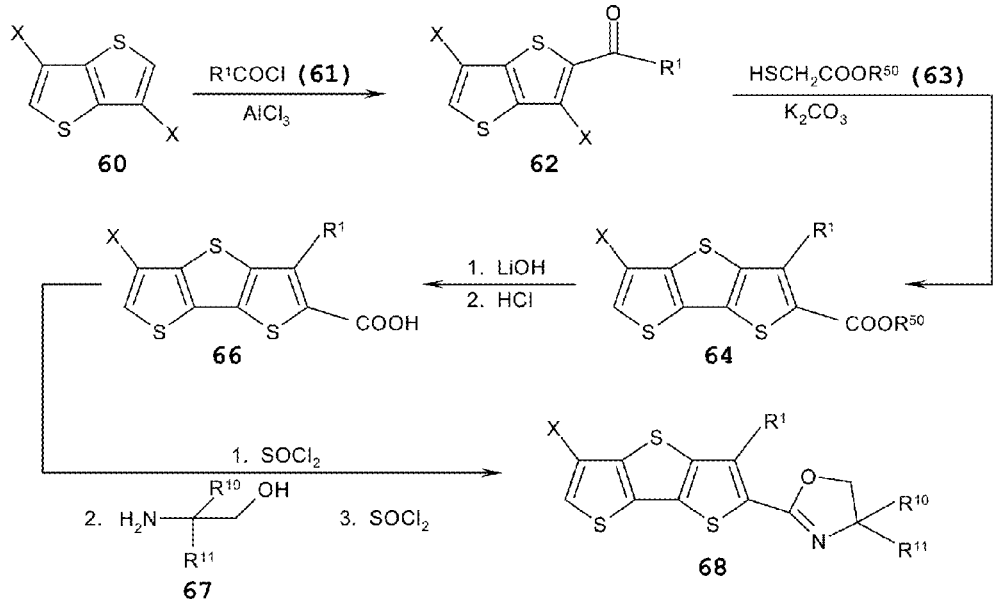

As further illustration, compounds having formula 11 can be prepared following the procedures described in FIG. 1B. Referring to FIG. 1B, thienothiophene 60 (e.g., dibromothienothiophene) can be reacted with an acid chloride (e.g., acid chloride 61), for example, in the presence of AlCl$_3$ or other Friedel-Crafts compatible Lewis acid (e.g., a stoichiometric amount of AlCl$_3$), to produce ketone 62. Ketone 62 can be converted to dithienothiophene ester 64, for example, by reaction with 2-mercaptoacetate 63 (e.g., in which $R^{50}$ is an alkyl or aryl group, such as an ethyl group or another unsubstituted C1-C4 alkyl group) in the presence of potassium carbonate or another base. Dithienothiophene ester 64 can be converted to dithienothiophene free acid 66, for example by hydrolyzing dithienothiophene ester 64 in the presence of lithium hydroxide, followed by acidification (e.g., with hydrochloric acid). Dithienothiophene free acid 66 can be converted to oxazolinyl dithienothiophene 68 by converting the free acid to the corresponding acid chloride (using, for example, thionyl chloride, oxalyl chloride, etc.), followed by reaction of the acid chloride with 1-amino-2-hydroxyalkane 67 (e.g., in which $R^{10}$ and $R^{11}$ are the same or different and are selected from hydrogen, alkyl, and aryl or in $R^{10}$ and $R^{11}$, together with the carbon atom to which they are bound, form a ring, for example as described above), followed by treatment with a dehydrating agent, such as thionyl chloride, phosphorus pentoxide, oxalyl chloride, and the like.

It should be noted that the X groups in the beta positions of thiophene 50 and thienothiophene 60 can be the same or they can be different. Illustratively, both X moieties can be the same halogen, as in the case where both X's are Br. Alternatively, the two X moieties can be different, as in the case where both one X is Br and the other X is F or as in the case where one X is a halogen (e.g., Br) and the other X is, for example, a triflate group.

The aforementioned compounds having formula 11 or 12 can be used in a variety of synthetic and other procedures, examples of which will be apparent from the discussion that follows.

The present invention, in another aspect thereof, relates to a compound having one of the following formulae 14, 15, 16, or 17:

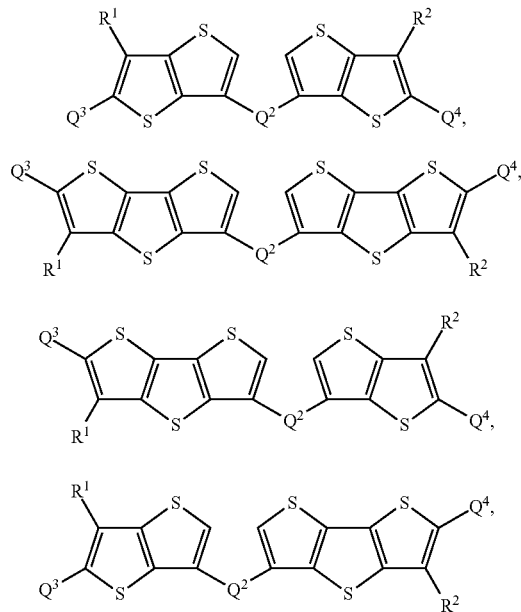

14

15

16

17 wherein $R^1$ and $R^2$ are the same or different and are selected from hydrogen, alkyl, and aryl; $Q^3$ and $Q^4$ are independently selected from hydrogen, a carboxylic acid, a carboxylic acid derivative, an alkyl group, an aryl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, or a halide; and $Q^2$ has one of the following formulae 18, 19, 20, 21A, or 21B:

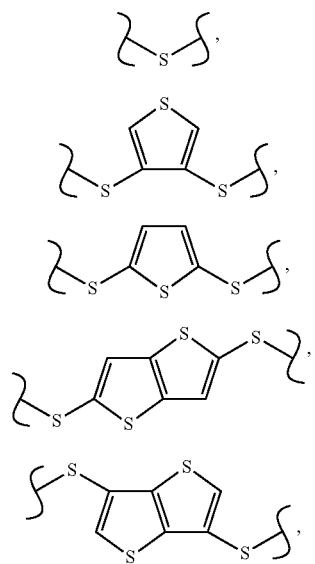

18

19

20

21A

21B or one of the following formulae 22A, 22B, 22C, 22D, or 22E:

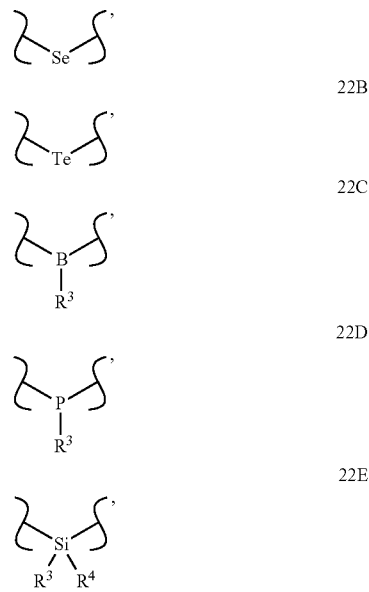

22A

22B

22C

22D

22E wherein $R^3$ and $R^4$ are the same or different and are selected from alkyl and aryl.

Illustratively, examples of such compounds include those set forth below:

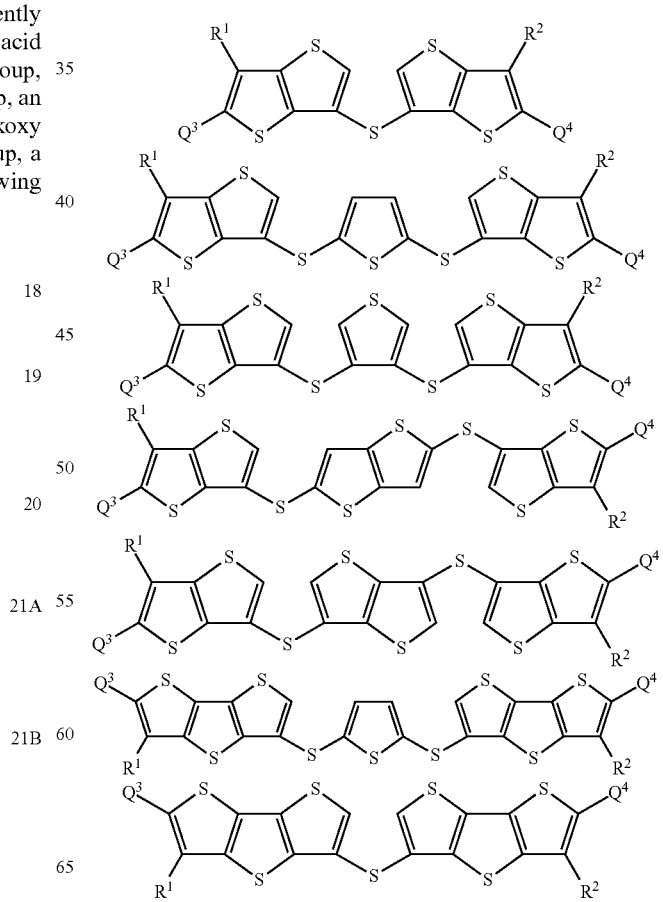

-continued
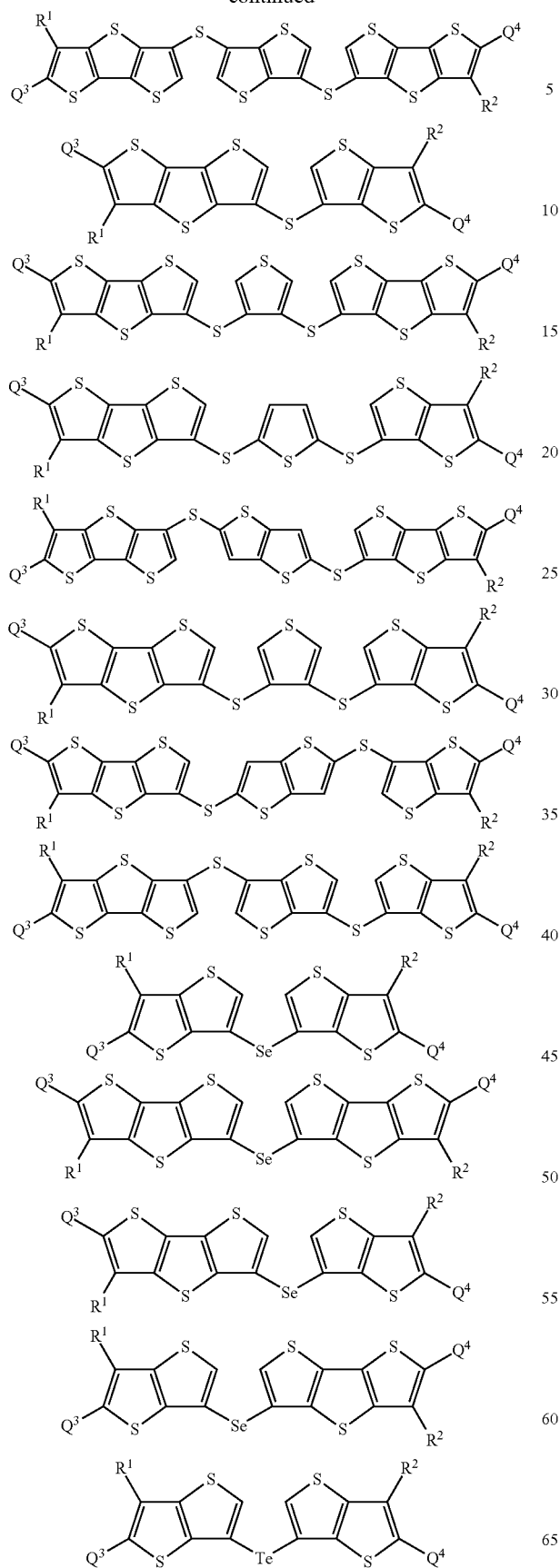
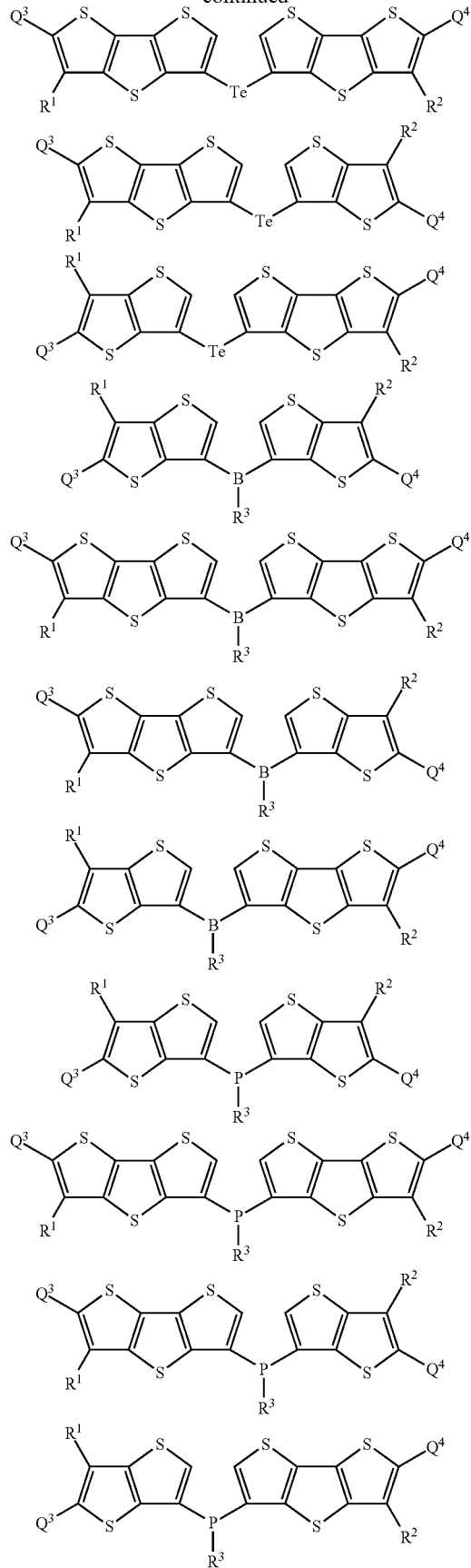

-continued

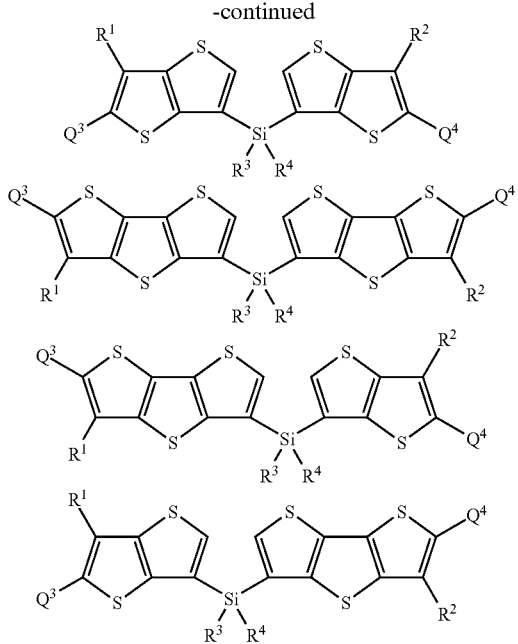

In certain embodiments, $Q^3$ and $Q^4$ are the same. In certain embodiments, $Q^3$ and $Q^4$ are different. In certain embodiments, $Q^3$, $Q^4$, or both $Q^3$ and $Q^4$ can be an aldehyde group or an aldehyde derivative. Examples of aldehyde derivatives include aldehyde protecting groups, such as acetals (e.g., cyclic acetals). In certain embodiments, $Q^3$, $Q^4$, or both $Q^3$ and $Q^4$ can be a carboxylic acid or a carboxylic acid derivative. Examples of carboxylic acid derivatives include carboxylic acid esters (e.g., substituted alkyl esters, unsubstituted alkyl esters, substituted C1-C6 alkyl esters, unsubstituted C1-C6 alkyl esters, substituted aryl esters, unsubstituted aryl esters, etc.); carboxylic acid amides (e.g., unsubstituted amides, monosubstituted amides, disubstituted amides, etc.); acyl halides (e.g., acyl chlorides, etc.); carboxyl protecting groups; and the like. In certain embodiments, $Q^3$, $Q^4$, or both $Q^3$ and $Q^4$ can be a carboxyl protecting group. Examples of carboxyl protecting groups include esters, thioesters, and oxazolines. As particular examples, there can be mentioned linear alkyl esters (e.g., linear C1-C8 alkyl esters, such as methyl esters, for example, where $Q^3$, $Q^4$, or both $Q^3$ and $Q^4$ are —COOCH$_3$); tertiary alkyl esters (e.g., tertiary C4-C8 alkyl esters, such as t-butyl esters, for example, where $Q^3$, $Q^4$, or both $Q^3$ and $Q^4$ are —COOC(CH$_3$)$_3$); aralkyl esters (e.g., (C6-C10)aryl-substituted-(C1-C4)alkyl esters, such as benzyl esters, for example, where $Q^3$, $Q^4$, or both $Q^3$ and $Q^4$ are —COOCH$_2$(C$_6$H$_5$)); and tertiary alkyl thioesters (e.g., tertiary C4-C8 alkyl thioesters, such as t-butyl thioesters, for example, where $Q^3$, $Q^4$, or both $Q^3$ and $Q^4$ are —C(O)SC(CH$_3$)$_3$). As noted above, $Q^3$, $Q^4$, or both $Q^3$ and $Q^4$ can be an oxazoline moiety, such as a 1,3-oxazolin-2-yl moiety, for example, as in the case where $Q^3$, $Q^4$, or both $Q^3$ and $Q^4$ have the formula:

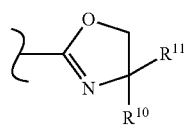

in which $R^{10}$ and $R^{11}$ are the same or different and are selected from hydrogen, alkyl (e.g., a substituted or unsubstituted C1-C8 alkyl), and aryl (e.g., a substituted or unsubstituted phenyl) or $R^{10}$ and $R^{11}$, together with the carbon atom to which they are bound, form a ring (e.g., a 4- to 8-membered (such as a 5-membered, 6-membered, etc.) homocyclic or heterocyclic ring). Illustratively, $R^{10}$ and $R^{11}$ can be the same or different lower alkyl, such as in the case where $R^{10}$ and $R^{11}$ are the same or different and are selected from a C1-C6 alkyl. In certain embodiments, $R^{10}$ and $R^{11}$ are the same lower alkyl, for example as in the case where each of $R^{10}$ and $R^{11}$ is a methyl group, an ethyl group, a n-propyl group, and i-propyl group, etc.

As noted above, $R^1$ and $R^2$ can be the same or different, each being independently selected from a hydrogen, an alkyl group, or an aryl group. Illustratively, $R^1$ and/or $R^2$ can be a variety of substituted or unsubstituted alkyl groups. For example, $R^1$ and/or $R^2$ can be an unsubstituted alkyl group, such as a straight-chain alkyl group (e.g. methyl, ethyl, propyl, butyl, pentyl, hexyl, heptyl, octyl, nonyl, decyl, undecyl, dodecyl or hexadecyl), a branched alkyl group (e.g. sec-butyl, neo-pentyl, 4-methylpentyl), or a substituted or unsubstituted cycloalkyl group (e.g. cyclopentyl, cyclohexyl). In certain embodiments, $R^1$ and/or $R^2$ is an alkyl group at least four carbons in size. In certain embodiments, $R^1$ and/or $R^2$ is a substituted alkyl group at least four carbons in size. In certain embodiments, $R^1$ and/or $R^2$ is a substituted alkyl group at least four carbons in size in which substitution of the alkyl group is separated from the fused thiophene ring system by at least two carbons. In certain embodiments, $R^1$ and/or $R^2$ is an alkyl group substituted with an aryl group, cycloalkyl group, aralkyl group, an alkenyl group, an alkynyl group, an amino group, an ester, an aldehyde, a hydroxyl group, an alkoxy group, a thiol group, a thioalkyl group, a halide, an acyl halide, an acrylate, or a vinyl ether. Examples of substituted alkyl groups include, but are not limited to, 6-hydroxyhexyl and 3-phenylbutyl. In certain embodiments, both $R^1$ and $R^2$ are hydrogen atoms. In certain embodiments, $R^1$ is a hydrogen atom, and $R^2$ is an alkyl group, such as one of the alkyl groups mentioned above. In certain embodiments, $R^2$ is a hydrogen atom, and $R^1$ is an alkyl group, such as one of the alkyl groups mentioned above. In certain embodiments both $R^1$ and $R^2$ are the same alkyl group. In certain embodiments $R^1$ represents one alkyl group, $R^2$ represents a different alkyl group. As with the selection of $R^1$ in the context of compounds having the formula 11 or 12, selection of $R^1$ and/or $R^2$ here can depend on the end use of the compound. The methods described herein permit the synthesis of fused thiophene moieties having a wide variety of $R^1$ and $R^2$ substituents. Any functionality that might be present on a substituted alkyl or aryl $R^1$ or $R^2$ group can be protected, for example, in order to survive subsequent reaction steps.

As noted above, $R^3$ and $R^4$ can be the same or different, and each is independently selected from an alkyl group or an aryl group. Illustratively, Wand/or Rican be a substituted alkyl group, an unsubstituted alkyl group, a substituted aryl group, or an unsubstituted aryl group. Suitable examples of $R^3$ and $R^4$ groups include those mentioned above with regard to $R^1$ and $R^2$.

The aforementioned compounds having formulae 14, 15, 16, or 17 can be prepared by any suitable method.

Figure 2A:
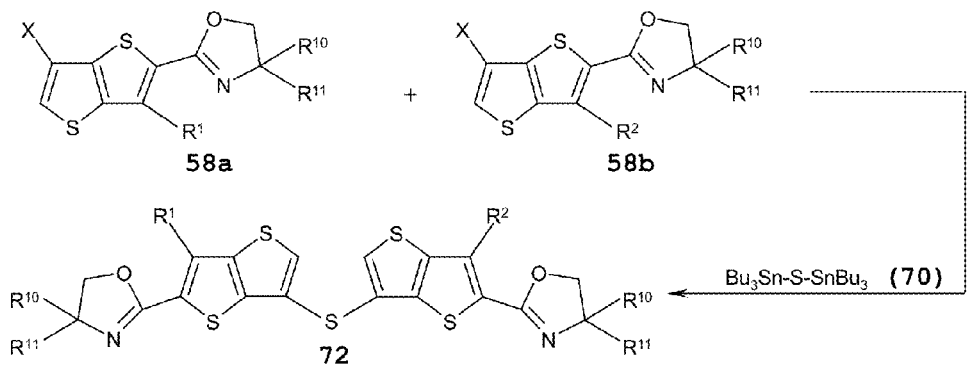
FIGS. 2A-2C are synthetic schemes that can be used to prepare certain compounds of the present invention.
Figure 2B:
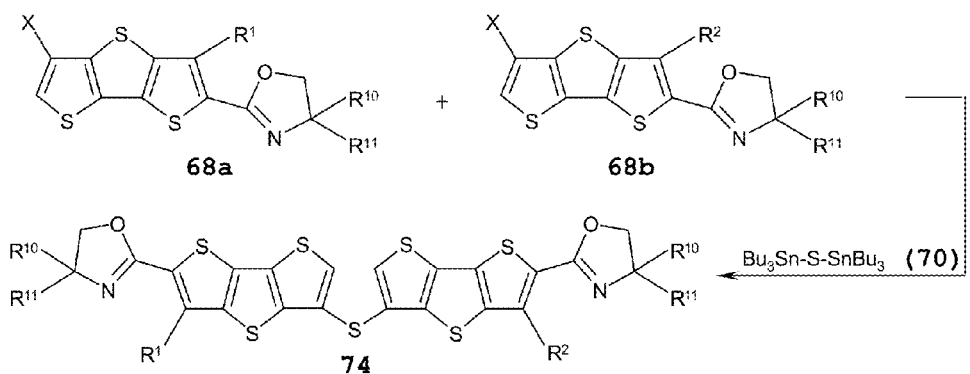

For example, compounds having formula 14 in which $Q^2$ has formula 18 can be prepared following the procedures described in FIG. 2A from compounds of the present invention having formula 12 and a bis(trialkyltin) sulfide, such as a bis(tri(C2-C6)alkyltin) sulfide, a bis(tri(C3-C4)alkyltin) sulfide, and/or a bis(tributyltin) sulfide. Referring to FIG. 2A, oxazolinyl thienothiophenes 58a and 58b (each of which can be separately prepared in accordance with the procedures described in FIG. 1A) are reacted with bis(tributyltin) sulfide 70 to produce compound 72. Compounds having formula 15 in which $Q^2$ has formula 18 can be prepared following the procedures described in FIG. 2B from compounds of the present invention having formula 11 and a bis(trialkyltin) sulfide, such as those mentioned above. Referring to FIG. 2B, oxazolinyl dithienothiophenes 68a and 68b (each of which can be separately prepared in accordance with the procedures described in FIG. 1B) can be reacted with bis(tributyltin) sulfide 70 to produce compound 74. Although the reaction schemes set forth in FIGS. 2A and 2B describe the use of bis(tributyltin) sulfide 70, other chemistries can be employed, such as where preparation of 82 from 58a and 58b or preparation of 86 from 68a and 68b is effected by reaction with butyl lithium (or another alkyl lithium reagent) followed by reaction of the resulting beta anion with a bis(arylsulfonyl) sulfide, such as a bis(phenylsulfonyl)sulfide (e.g., $(PhSO_2)_2$ S), for example, using procedures analogous to those described in PCT Patent Application Publication No. WO 2006/031893 and He et al., *J. Org. Chem.*, 72(2):444-451 (2007), which are hereby incorporated by reference.

Figure 2C:
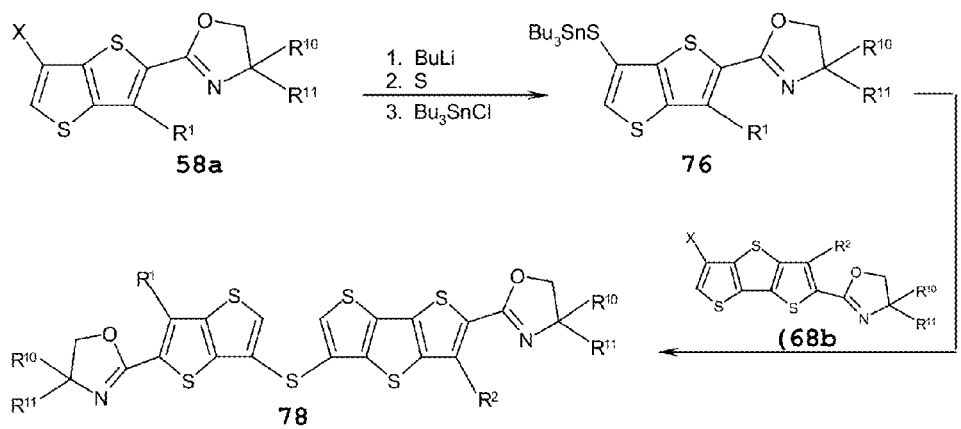

As further illustration, compounds having formula 16 or 17 in which $Q^2$ has formula 18 can be prepared following the procedures described in FIG. 2C from compounds of the present invention having formula 11 and 12. Referring to FIG. 2C, oxazolinyl thienothiophene 58a (which can be prepared in accordance with the procedures described in FIG. 1A) is reacted with an alkyl lithium compound (e.g., butyl lithium), followed by reaction with sulfur and then with a trialkyl tin halide (e.g., tributyl tin chloride) to produce tin sulfide thienothiophene 76. Tin sulfide thienothiophene 76 can then be reacted with oxazolinyl dithienothiophene 68b (which can be prepared in accordance with the procedures described in FIG. 1B) to produce compound 78.

Figure 3A:
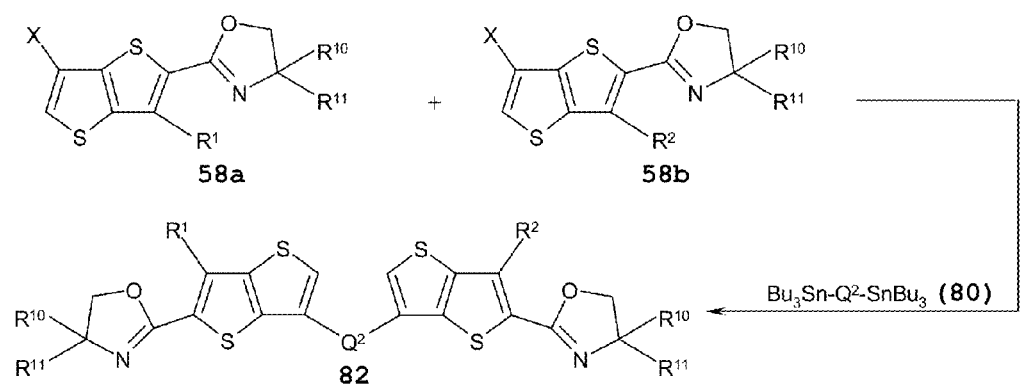
FIGS. 3A and 3B are synthetic schemes that can be used to prepare certain compounds of the present invention.

As yet further illustration, compounds having formula 14 in which $Q^2$ has formula 19, 20, 21A, or 21B can be prepared following the procedures described in FIG. 3A from compounds of the present invention having formula 12 and a di(trialkyltin sulfide) thiophene or a di(trialkyltin sulfide) thienothiophene, such as a di(tri(C2-C6)alkyltin sulfide) thiophene or a di(tri(C2-C6)alkyltin sulfide) thienothiophene, a di(tri(C3-C4)alkyltin sulfide) thiophene or a di(tri(C3-C4)alkyltin sulfide) thienothiophene, and/or a di(tributyltin sulfide) thiophene or a di(tributyltin sulfide) thienothiophene. Referring to FIG. 3A, oxazolinyl thienothiophenes 58a and 58b (each of which can be separately prepared in accordance with the procedures described in FIG. 1A) are reacted with di(trialkyltin sulfide) thiophene or di(trialkyltin sulfide) thienothiophene 80 to produce compound 82.

Figure 3B:
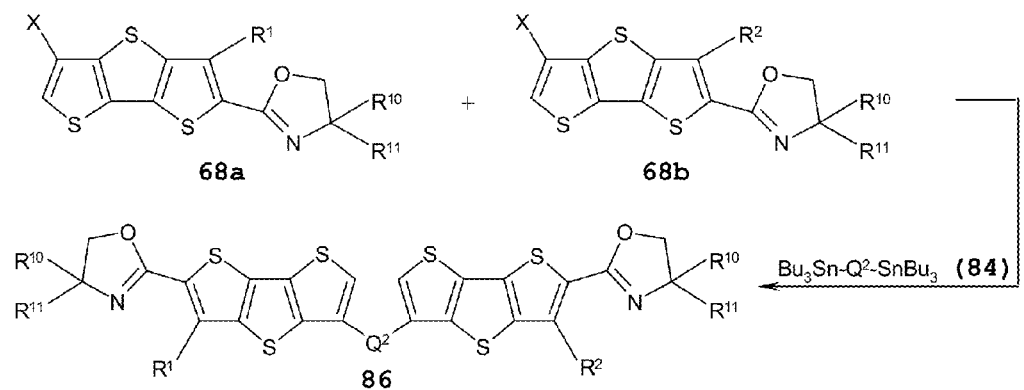

As still further illustration, compounds having formula 15 in which $Q^2$ has formula 19, 20, 21A, or 21B can be prepared following the procedures described in FIG. 3B from compounds of the present invention having formula 11 and a di(trialkyltin sulfide) thiophene or a di(trialkyltin sulfide) thienothiophene, such as those mentioned above. Referring to FIG. 3B, oxazolinyl dithienothiophene 68a and 68b (each of which can be separately prepared in accordance with the procedures described in FIG. 2A) are reacted with di(trialkyltin sulfide) thiophene or di(trialkyltin sulfide) thienothiophene 84 to produce compound 86.

The reaction schemes set forth in FIGS. 3A and 3B make use of di(trialkyltin sulfide) thiophene or di(trialkyltin sulfide) thienothiophene 80 and 84. Preparative schemes for making these di(trialkyltin sulfide) thiophenes and di(trialkyltin sulfide) thienothiophene are described below.

As still further illustration, compounds having formula 14 in which $Q^2$ has formula 22A, 22B, 22C, 22D, or 22E can be prepared from compounds of the present invention having formula 12 following procedures similar to that described in FIG. 3A; and compounds having formula 15 in which $Q^2$ has formula 22A, 22B, 22C, 22D, or 22E can be prepared from compounds of the present invention having formula 11 following procedures similar to that described in FIG. 3B. More particularly, a compound of the present invention having formula 12 (e.g., oxazolinyl dithienothiophene 58a and 58b (each of which can be separately prepared in accordance with the procedures described in FIG. 1A)) or a compound of the present invention having formula 11 (e.g., oxazolinyl dithienothiophene 68a and 68b (each of which can be separately prepared in accordance with the procedures described in FIG. 1B)) can be treated with butyl lithium (or another alkyl lithium) to produce the corresponding beta anion, and the resulting beta anion can then be reacted with an appropriate reagent, such as a selenium dihalide (e.g., $SeCl_2$) to produce compounds having formula 14 or 15 in which $Q^2$ has formula 22A; a tellurium dihalide (e.g., $TeCl_2$) to produce compounds having formula 14 or 15 in which $Q^2$ has formula 22B; an alkyl or aryl boron dihalide (e.g., $R^3BCl_2$, in which $R^3$ is an alkyl or aryl group) to produce compounds having formula 14 or 15 in which $Q^2$ has formula 22C; a dihalo alkyl phosphine or dihalo aryl phosphine (e.g., $R^3PBr_2$, in which $R^3$ is an alkyl or aryl group) to produce compounds having formula 14 or 15 in which $Q^2$ has formula 22D; or a dihalo dialkyl silane, a dihalo diaryl silane, or a dihalo alkyl aryl silane (e.g., $R^3R^4SiCl_2$, in which $R^3$ and $R^4$ are the same or different and represent an alkyl or aryl group) to produce compounds having formula 14 or 15 in which $Q^2$ has formula 22E.

In all of the reaction schemes discussed above (e.g., those set forth in FIGS. 2A-2C and 3A-3B), the product is shown to have terminal thiophene rings bearing an oxazoline moiety in the alpha position (i.e., compounds having formula 14, 15, 16, or 17 in which $Q^3$ and $Q^4$ are an oxazoline groups). As one skilled in the art will recognize, an oxazoline group can be readily converted to the carboxylic acid (for example, by treatment with HCl or another strong acid), and the carboxylic acid can be converted to esters, amides, and other carboxylic acid derivatives using conventional procedures. These carboxylic acids and carboxylic acid derivatives can then be converted to hydrogen (e.g., compounds having formula 14, 15, 16, or 17 in which $Q^3$ and $Q^4$ are hydrogen atoms) or other functional groups, such as those described above.

The aforementioned compounds having formulae 14, 15, 16, or 17 can be used in a variety of synthetic and other procedures, examples of which will be apparent from the discussion that follows.

The present invention, in another aspect thereof, relates to a compound having the formula:

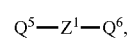

23 wherein $Z^1$ has one of the following formulae 24A, 24B, 24C, 24D, 25, 26, 27, 28, 29, or 30:

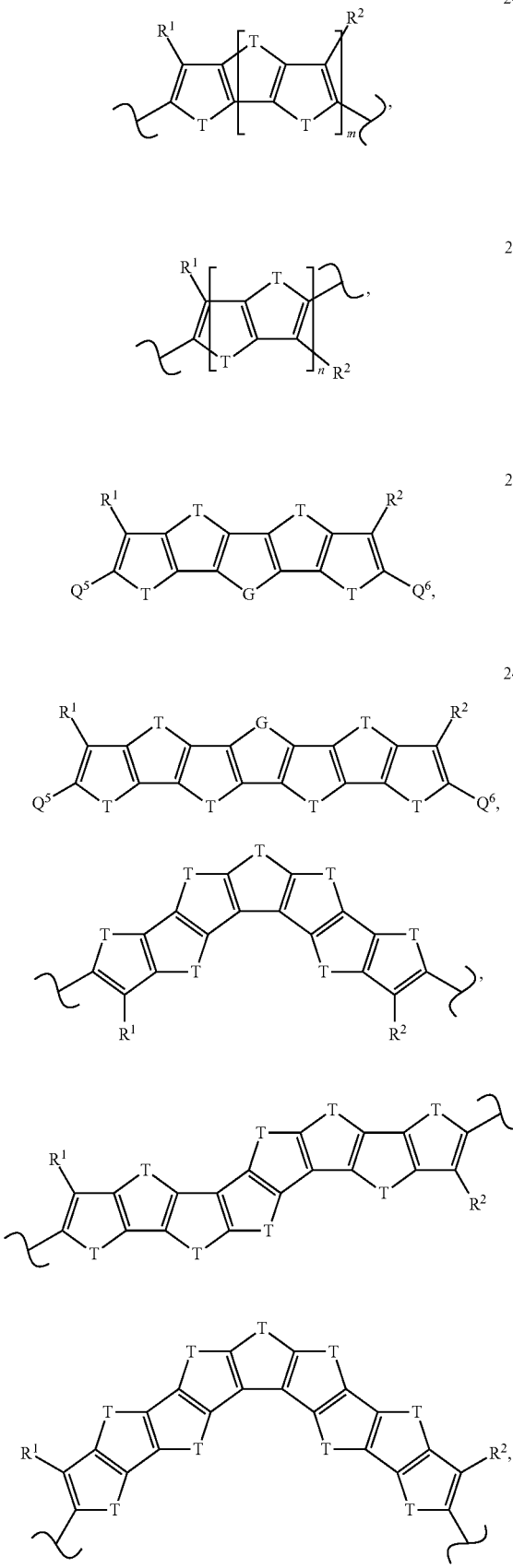

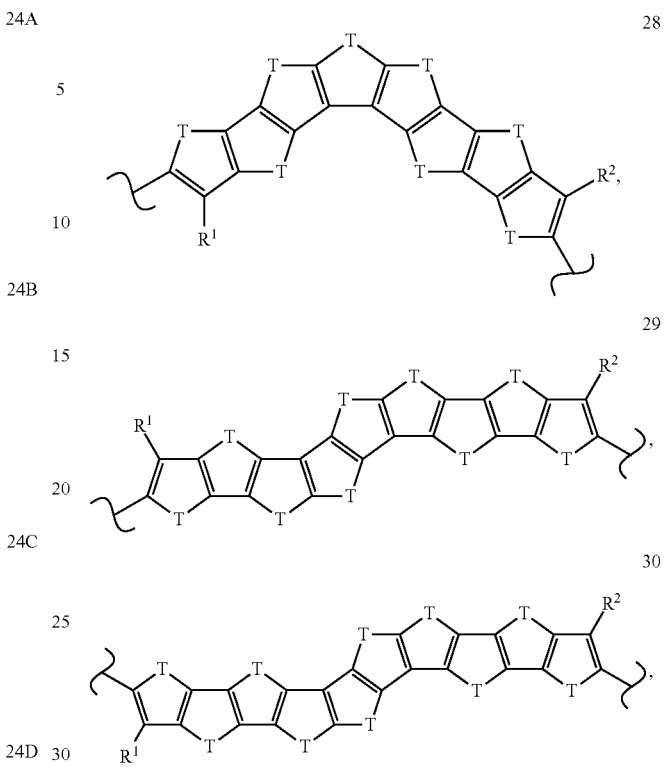

wherein n is 3, 4, or 5; m is 2, 3, or 4; G is selected from —Se—, —Te—, —B($R^3$)—, —P($R^3$)—, and —Si($R^3$)($R^4$)—; each T is independently selected from S and $SO_2$; $R^1$ and $R^2$ are the same or different and are selected from hydrogen, alkyl, and aryl; $Q^5$ and $Q^6$ are the same or different and are selected from hydrogen, a carboxylic acid, a carboxylic acid derivative, an alkyl group, an aldehyde derivative, an aryl group, an aldehyde group, a ketone group, a hydroxyl group, an unsubstituted thiol group, a substituted thiol group, an alkoxy group, an acrylate group, an amino group, a vinyl group, a vinyl ether group, or a halide, provided that, when $Z^1$ has formula 24A or 24B, at least one of $Q^5$ and $Q^6$ is a thioester, an oxazoline moiety, or an acetal.

Illustratively, examples of compounds of formula 23 in which $Z^1$ has formula 24A include those set forth below:

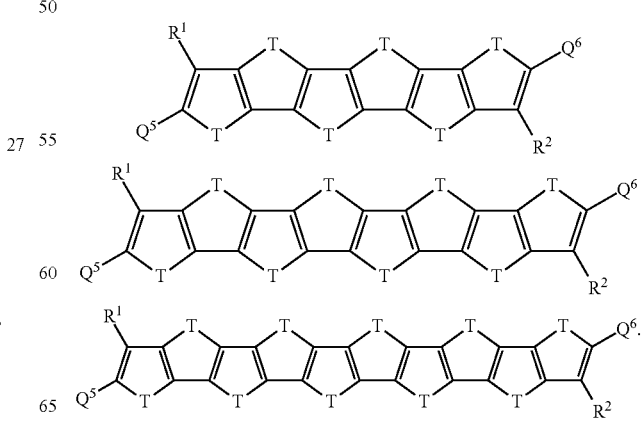

Illustrative examples of compounds of formula 23 in which $Z^1$ has formula 24B include those set forth below:

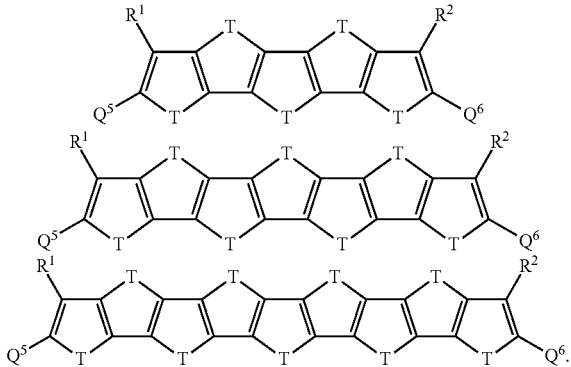

Illustrative examples of compounds of formula 23 in which $Z^1$ has formula 24C include those set forth below:

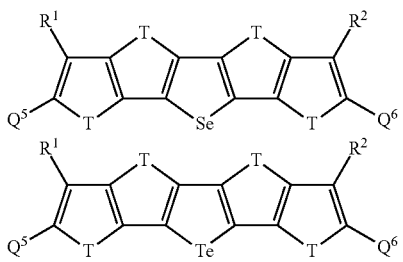

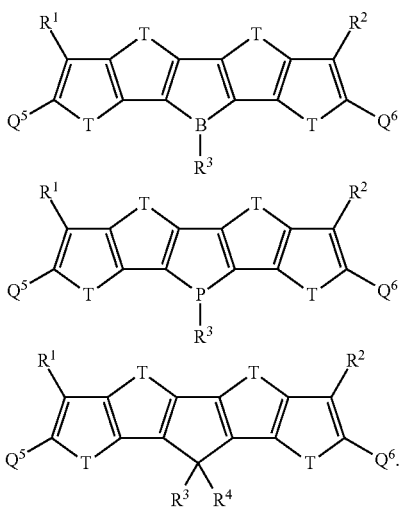

Illustrative examples of compounds of formula 23 in which $Z^1$ has formula 24C include those set forth below:

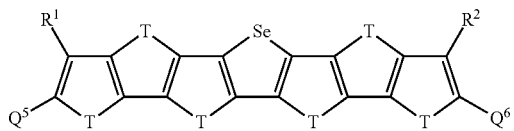

-continued

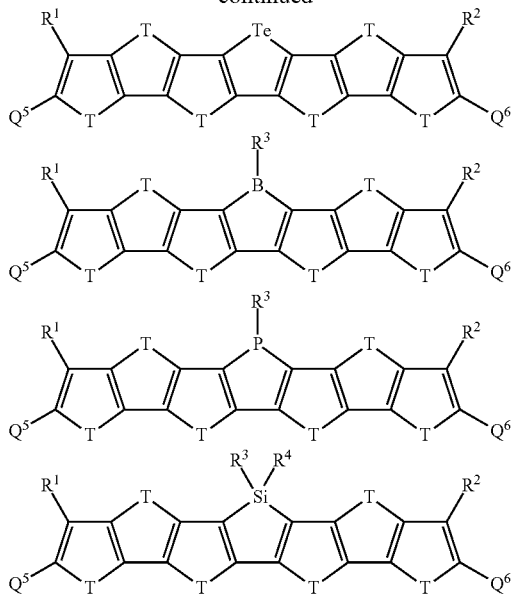

As noted above, $R^1$ and $R^2$ can be the same, or they can be different; and each is independently selected from a hydrogen, an alkyl group, or an aryl group. Illustratively, $R^1$ and/or $R^2$ can be a variety of substituted or unsubstituted alkyl groups. For example, $R^1$ and/or $R^2$ can be an unsubstituted alkyl group, such as a straight-chain alkyl group (e.g. methyl, ethyl, propyl, butyl, pentyl, hexyl, heptyl, octyl, nonyl, decyl, undecyl, dodecyl or hexadecyl), a branched alkyl group (e.g. sec-butyl, neo-pentyl, 4-methylpentyl), or a substituted or unsubstituted cycloalkyl group (e.g. cyclopentyl, cyclohexyl). In certain embodiments, $R^1$ and/or $R^2$ is an alkyl group at least four carbons in size. In certain embodiments, $R^1$ and/or $R^2$ is a substituted alkyl group at least four carbons in size. In certain embodiments, $R^1$ and/or $R^2$ is a substituted alkyl group at least four carbons in size in which substitution of the alkyl group is separated from the fused thiophene ring system by at least two carbons. In certain embodiments, $R^1$ and/or $R^2$ is an alkyl group substituted with an aryl group, cycloalkyl group, aralkyl group, an alkenyl group, an alkynyl group, an amino group, an ester, an aldehyde, a hydroxyl group, an alkoxy group, a thiol group, a thioalkyl group, a halide, an acyl halide, an acrylate, or a vinyl ether. Examples of substituted alkyl groups include, but are not limited to, 6-hydroxyhexyl and 3-phenylbutyl. In certain embodiments, both $R^1$ and $R^2$ are hydrogen atoms. In certain embodiments, $R^1$ is a hydrogen atom, and $R^2$ is an alkyl group, such as one of the alkyl groups mentioned above. In certain embodiments, $R^2$ is a hydrogen atom, and $R^1$ is an alkyl group, such as one of the alkyl groups mentioned above. In certain embodiments both $R^1$ and $R^2$ are the same alkyl group. In certain embodiments $R^1$ represents one alkyl group, $R^2$ represents a different alkyl group. As with the selection of $R^1$ in the context of compounds having the formula 11 or 12, selection of $R^1$ and/or $R^2$ here can depend on the end use of the compound. The methods described herein permit the synthesis of fused thiophene moieties having a wide variety of $R^1$ and $R^2$ substituents, and any functionality that might be present on a substituted alkyl or aryl $R^1$ or $R^2$ group can be protected, for example, in order to survive subsequent reaction steps.

In certain embodiments, each T is S (i.e., a sulfur atom). In certain embodiments, at least one T is $SO_2$. In certain embodiments, at least one of the three or four central-most T's is $SO_2$ and the remaining T's are S, for example, as in the case where the compound has formula 24A, 26, 28, or 30, at least one (e.g., one, two, three, or four) of the four central-most T's is $SO_2$, and the remaining T's are S; and as in the case where the compound has formula 24B, 25, 27, or 29, at least one (e.g., one, two, or three) of the three central-most T's is $SO_2$, and the remaining T's are S.

In certain embodiments, each T is independently S or $SO_2$, where T is $SO_2$ in at least one of the central-most rings of the fused thiophene ring system.

As used herein, the central-most ring of a fused thiophene ring system having an odd number 2q+1 of fused rings is the q+1$^{th}$ ring from an end of the ring system. The central-most rings of a fused thiophene ring system having an even number 2q of fused rings are the q$^{th}$ and q+1$^{th}$ rings from an end of the ring system. For example, the central-most ring of a five-ring system is the third ring, the central-most rings of a six-ring system are the third and fourth rings, and the central-most ring of a seven-ring system is the fourth ring.

In certain embodiments, $Z^1$ has one of the formulae 24A or 24B. In such embodiments, at least one of $Q^5$ and $Q^6$ is a thioester, an oxazoline, or an acetal. For example, in certain such embodiments, each of $Q^5$ and $Q^6$ is a thioester or an oxazoline, and $Q^5$ and $Q^6$ are the same. In certain embodiments, each of $Q^5$ and $Q^6$ is an oxazoline, and $Q^5$ and $Q^6$ are the same. In certain embodiments, each of $Q^5$ and $Q^6$ is an acetal, and $Q^5$ and $Q^6$ are the same. In certain embodiments, one of $Q^5$ and $Q^6$ is a thioester, an oxazoline, or an acetal; and the other of $Q^5$ and $Q^6$ is hydrogen, a carboxylic acid, a carboxylic acid derivative, an alkyl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, or a halide. In certain embodiments, at least one of $Q^5$ and $Q^6$ is an oxazoline moiety, such as a 1,3-oxazolin-2-yl moiety, for example, as in the case where at least one of $Q^5$ and $Q^6$ has the formula:

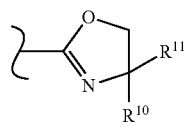

in which $R^{10}$ and $R^{11}$ are the same or different and are selected from hydrogen, alkyl (e.g., a substituted or unsubstituted C1-C8 alkyl), and aryl (e.g., a substituted or unsubstituted phenyl) or $R^{10}$ and $R^{11}$, together with the carbon atom to which they are bound, form a ring (e.g., a 4- to 8-membered (such as a 5-membered, 6-membered, etc.) homocyclic or heterocyclic ring). Illustratively, $R^{10}$ and $R^{11}$ can be the same or different lower alkyl, such as in the case where $R^{10}$ and $R^{11}$ are the same or different and are selected from a C1-C6 alkyl. In certain embodiments, $R^{10}$ and $R^{11}$ are the same lower alkyl, for example as in the case where each of $R^{10}$ and $R^{11}$ is a methyl group, an ethyl group, a n-propyl group, and i-propyl group, etc.

In certain embodiments, $Z^1$ has one of the formulae 24C, 24D, 25, 26, 27, 28, 29, or 30. In such embodiments, $Q^5$ and $Q^6$ are the same or different and are selected from hydrogen, a carboxylic acid, a carboxylic acid derivative, an alkyl group, an aryl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, or a halide.

By way of illustration, in certain such embodiments, $Q^5$ and $Q^6$ are the same. In certain embodiments, $Q^5$ and $Q^6$ are different. In certain embodiments, at least one of $Q^5$ and $Q^6$ is a hydrogen, such as in the case where each of $Q^5$ and $Q^6$ is a hydrogen. In certain embodiments, at least one of $Q^5$ and $Q^6$ is an aldehyde group, such as in the case where each of $Q^5$ and $Q^6$ is an aldehyde group. In certain embodiments, at least one of $Q^5$ and $Q^6$ is an aldehyde derivative, such as in the case where each of $Q^5$ and $Q^6$ is an aldehyde derivative. Examples of aldehyde derivatives include aldehyde protecting groups, such as acetals (e.g., cyclic acetals). In certain embodiments, at least one of $Q^5$ and $Q^6$ is a carboxylic acid, such as in the case where each of $Q^5$ and $Q^6$ is a carboxylic acid. In certain embodiments, at least one of $Q^5$ and $Q^6$ is a carboxylic acid derivative, such as in the case where each of $Q^5$ and $Q^6$ is a carboxylic acid derivative. Examples of carboxylic acid derivatives include carboxylic acid esters (e.g., substituted alkyl esters, unsubstituted alkyl esters, substituted C1-C6 alkyl esters, unsubstituted C1-C6 alkyl esters, substituted aryl esters, unsubstituted aryl esters, etc.); carboxylic acid amides (e.g., unsubstituted amides, monosubstituted amides, disubstituted amides, etc.); acyl halides (e.g., acyl chlorides, etc.); carboxyl protecting groups; and the like. In certain embodiments, at least one of $Q^5$ and $Q^6$ is a carboxyl protecting group, such as in the case where each of $Q^5$ and $Q^6$ is a carboxyl protecting group. Examples of carboxyl protecting groups include esters, thioesters, and oxazolines. As particular examples, there can be mentioned linear alkyl esters (e.g., linear C1-C8 alkyl esters, such as methyl esters, for example, where $Q^5$, $Q^6$, or both $Q^5$ and $Q^6$ are —$COOCH_3$); tertiary alkyl esters (e.g., tertiary C4-C8 alkyl esters, such as t-butyl esters, for example, where $Q^5$, $Q^6$, or both $Q^5$ and $Q^6$ are —$COOC(CH_3)_3$); aralkyl esters (e.g., (C6-C10)aryl-substituted-(C1-C4)alkyl esters, such as benzyl esters, for example, where $Q^5$, $Q^6$, or both $Q^5$ and $Q^6$ are —$COOCH_2(C_6H_5)$); and tertiary alkyl thioesters (e.g., tertiary C4-C8 alkyl thioesters, such as t-butyl thioesters, for example, where $Q^5$, $Q^6$, or both $Q^5$ and $Q^6$ are —$C(O)SC(CH_3)_3$). As noted above, $Q^5$, $Q^6$, or both $Q^5$ and $Q^6$ can be an oxazoline moiety, such as a 1,3-oxazolin-2-yl moiety, for example, as in the case $Q^5$, $Q^6$, or both $Q^5$ and $Q^6$ have the formula:

in which $R^{10}$ and $R^{11}$ are the same or different and are selected from hydrogen, alkyl (e.g., a substituted or unsubstituted C1-C8 alkyl), and aryl (e.g., a substituted or unsubstituted phenyl) or $R^{10}$ and $R^{11}$, together with the carbon atom to which they are bound, form a ring (e.g., a 4- to 8-membered (such as a 5-membered, 6-membered, etc.) homocyclic or heterocyclic ring). Illustratively, $R^{10}$ and $R^{11}$ can be the same or different lower alkyl, such as in the case where $R^{10}$ and $R^{11}$ are the same or different and are selected from a C1-C6 alkyl. In certain embodiments, $R^{10}$ and $R^{11}$ are the same lower alkyl, for example as in the case where each of $R^{10}$ and $R^{11}$ is a methyl group, an ethyl group, a n-propyl group, and i-propyl group, etc.

As noted above, when $Z^1$ has one of the formulae 24C, 24D, 25, 26, 27, 28, 29, or 30, $Q^5$ and $Q^6$ can be the same or different and selected from hydrogen, a carboxylic acid, a carboxylic acid derivative, an alkyl group, an aryl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, or a halide. These groups can be chosen, for example, based on the use to which the compound is to be put. By way of illustration, choice of $Q^5$ and $Q^6$ can be based, in whole or in part, on a group's ability to participate in subsequent reactions (e.g., polymerization reactions or cross-linking reactions), on a group's reactivity or inertness, on a group's ability to affect solubility of the compound in a particular solvent or class of solvents, and the like. By way of further illustration, $Q^5$ and $Q^6$ can be selected for their ability to function as electron donors and/or electron acceptors in donor-acceptor chromophores. For example, $Q^5$ and $Q^6$ can be chosen such that one of $Q^5$ and $Q^6$ is an electron donating group and the other of $Q^5$ and $Q^6$ is an electron accepting group, such as in the case where $Q^5$ is an electron donating group and $Q^6$ is an electron accepting group or as in the case where $Q^6$ is an electron donating group and $Q^5$ is an electron accepting group. The phrase "electron donating group" refers to substituents which contribute electron density to a compound's pi-electron system when the compound's electron structure is polarized by the input of electromagnetic energy. The phrase "electron accepting group" (which is sometimes used synonymously with "electron withdrawing group") refers to substituents which attract electron density to a compound's pi-electron system when the compound's electron structure is polarized by the input of electromagnetic energy. In this manner, for example, a compound of the present invention can be a donor-acceptor chromophore, the term "chromophore", as used herein, referring to an optical compound comprising an electron donating group and an electron accepting group at opposing termini of a conjugated pi electron system. Donor-acceptor chromophores, as well as suitable electron donating groups and electron accepting group, are described in U.S. Pat. No. 6,584,266 to He et al., U.S. Pat. No. 6,514,434 to He et al.; U.S. Pat. No. 6,448,416 to He et al.; U.S. Pat. No. 6,444,830 to He et al.; and U.S. Pat. No. 6,393,190 to He et al., which are hereby incorporated by reference.

In certain embodiments, $Z^1$ has one of the formulae 24C, 24D, 25, 26, 27, 28, 29, or 30, and $Q^5$ and $Q^6$ are chosen such that at least one of $Q^5$ and $Q^6$ is an aryl group having the following formula 31:

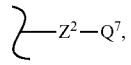

31 wherein $Z^2$ has one of formulae 24A, 24B, 24C, 24D, 25, 26, 27, 28, 29, or 30 and wherein $Q^7$ is selected from hydrogen, a carboxylic acid, a carboxylic acid derivative, an alkyl group, an aryl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, and a halide.

Illustrative of such compounds are those having the following formula 32:

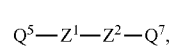

32

(i) in which $Z^1$ has one of the formulae 24C, 24D, 25, 26, 27, 28, 29, or 30 and $Z^2$ has one of formulae 24A or 24B, for example, compounds having the formulae:

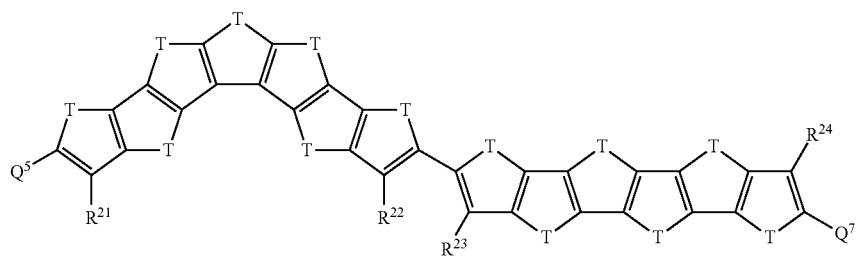

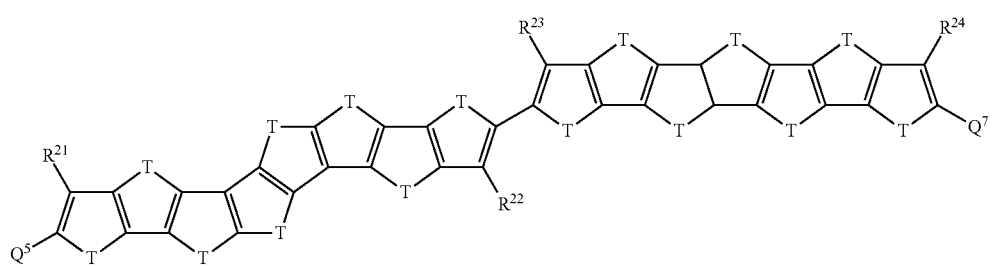

and (ii) in which $Z^1$ has one of the formulae 24C, 24D, 25, 26, 27, 28, 29, or 30 and $Z^2$ has one of formulae 24C, 24D, 25, 26, 27, 28, 29, or 30, for example, compounds having the formulae:

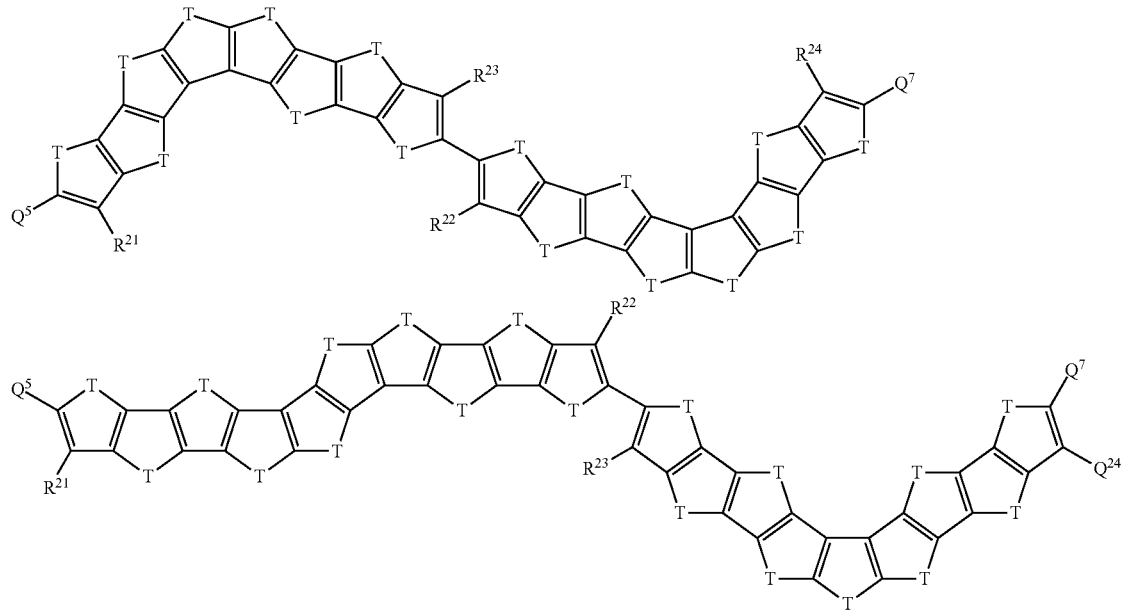

In the above formulae, $R^{21}$, $R^{22}$, $R^{23}$, and $R^{24}$ can be the same, or they can be different; and each is independently selected from the moieties recited above for $R^1$ and $R^2$ (i.e., hydrogen, an alkyl group, or an aryl group), and each T is independently selected from S and $SO_2$.

As will be apparent from the above discussion, $Z^1$ and $Z^2$ can be the same, or $Z^1$ and $Z^2$ can be different. Moreover, in cases where both $Q^5$ and $Q^6$ are aryl groups having formula 31, $Q^5$ and $Q^6$ can be the same (e.g., in cases where $Z^2$ and $Q^7$ is the same for each of $Q^5$ and $Q^6$); or $Q^5$ and $Q^6$ can be different (e.g., as in the case where $Q^5$'s $Z^2$ is different than $Q^6$'s $Z^2$ and/or where $Q^5$'s $Q^7$ is different than $Q^6$'s $Q^7$).

In certain embodiments, $Q^6$ is an aryl group having formula 31, and $Q^5$ and $Q^7$ are selected such that one of $Q^5$ and $Q^7$ is an electron donating group, and the other of $Q^5$ and $Q^7$ is an electron accepting group. In certain embodiments, $Q^5$ is an aryl group having formula 31, and $Q^6$ and $Q^7$ are selected such that one of $Q^6$ and $Q^7$ is an electron donating group and the other of $Q^6$ and $Q^7$ is an electron accepting group. In certain embodiments, both $Q^5$ and $Q^6$ are aryl groups having formula 31, for example, as in the case where the compound has the following formula 33:

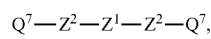

and the $Q^7$'s are selected such that one $Q^7$ is an electron donating group and the other $Q^7$ is an electron accepting group.

In certain embodiments, $Z^1$ has one of the formulae 24C, 24D, 25, 26, 27, 28, 29, or 30, and $Q^5$ and $Q^6$ are chosen such that at least one of $Q^5$ and $Q^6$ is an aryl group having the following formula 34:

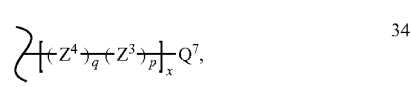

wherein each $Z^3$ is independently selected from formulae 24A, 24B, 24C, 24D, 25, 26, 27, 28, 29, and 30; each $Z^4$ is the same or different and is an aryl group; $Q^7$ is selected from hydrogen, a carboxylic acid, a carboxylic acid derivative, an alkyl group, an aryl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, and a halide; each p is the same or different and is zero or an integer greater than zero and each q is the same or different and is zero or an integer greater than zero, provided that at least one p or at least one q is not zero; and x is greater than or equal to one. Illustratively, aryl groups that can be used as $Z^4$ in the above formula 34 include aromatic rings that can undergo a Stille reaction. Examples of suitable $Z^4$ groups include benzene rings (e.g., a benzene ring bonded via the 1 and 4 positions); naphthalene rings (e.g., a naphthalene ring bonded via the 2 and 6 positions); heteroaryl rings, such as 5-membered heteroaryl rings, for example, thiophene rings (e.g., a thiophene ring bonded via the thiophene ring's alpha positions) and furan rings (e.g., a furan ring bonded via the furan ring's alpha positions). By way of further illustration of suitable $Z^4$ groups, there can be mentioned those of the following formulae:

-continued

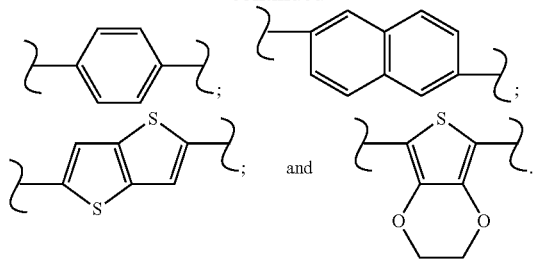

By way of illustration, suitable values for p include 0, 1, 2, 3, 4, 5, 6, 7, 8, 9, 10, 11, 12, 13, 14, from 15 to 20, from 20 to 50, from 50 to 100, and the like; suitable values for q include 0, 1, 2, 3, 4, 5, 6, 7, 8, 9, 10, 11, 12, 13, 14, from 15 to 20, from 20 to 50, from 50 to 100, and the like; and suitable values for x include 1, 2, 3, 4, 5, 6, 7, 8, 9, 10, 11, 12, 13, 14, from 15 to 20, from 20 to 50, from 50 to 100, from 100 to 200, from 200 to 500, from 500 to 1000, and the like;

For example, when x is one, the compound contains only one unit having the following formula:

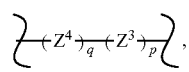

and there is only one p value and one q value. When x is greater than one, the compound contains more than one unit having formula 35, and the p values and the q values for each unit can be the same (e.g., as in the case where the units are repeating units) or the p values and/or the q values for each unit can be different (e.g., as in the case where the units are randomly-selected or otherwise non-repeating units).

When x is one, the compound contains only one unit having formula 35, and the number of $Z^3$ units is p. When p is one, there is only one $Z^3$ unit. When p is greater than one, there is more than one $Z^3$ unit, and these $Z^3$ units can be the same, or they can be different. Similarly, when x is one, the compound contains only one unit having formula 35, and the number of $Z^4$ units is q. When q is one, there is only one $Z^4$ unit. When q is greater than one, there is more than one $Z^4$ unit, and these $Z^4$ units can be the same, or they can be different.

When x is greater than one, the compound contains more than one unit having formula 35, the number of $Z^3$ units is x multiplied by p, and these $Z^3$ units can be the same, or they can be different. Similarly, when x is greater than one, the compound contains more than one unit having formula 35, the number of $Z^4$ units is x multiplied by q, and these $Z^4$ units can be the same, or they can be different.

For example, aryl groups having formula 34 are meant to include groups in which each q is zero, for example, as in the case where the aryl group has the following formula:

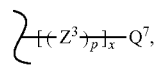

examples of which include:

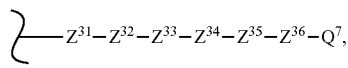

in which $Z^{31}$, $Z^{32}$, $Z^{33}$, $Z^{34}$, $Z^{35}$, and $Z^{36}$ are different from one another and selected from formulae 24A, 24B, 24C, 24D, 25, 26, 27, 28, 29, and 30. In certain embodiments, each q is zero, and each p is one. In certain embodiments, each q is zero, each p is one, and each $Z^3$ is the same.

As further illustration, aryl groups having formula 34 are meant to include groups in which each p is zero, for example, as in the case where the aryl group has the following formula:

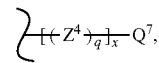

examples of which include:

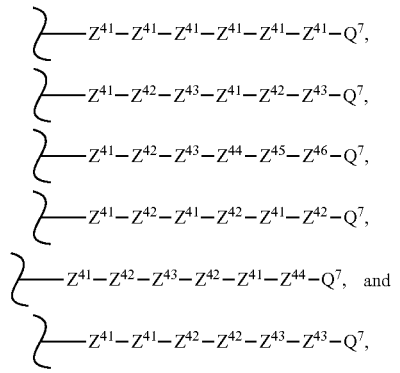

in which $Z^{41}$, $Z^{42}$, $Z^{43}$, $Z^{44}$, $Z^{45}$, and $Z^{46}$ are different from one another, each representing a different aryl group. In certain embodiments, each p is zero, and each q is one. In certain embodiments, each p is zero, each q is one, and each $Z^4$ is the same.

As still further illustration, aryl groups having formula 34 are meant to include groups in which at least one p is an integer greater than zero and in which at least one q is an integer greater than zero, examples of which include:

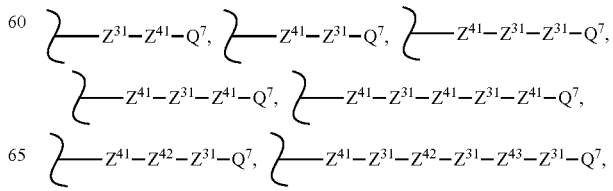

-continued

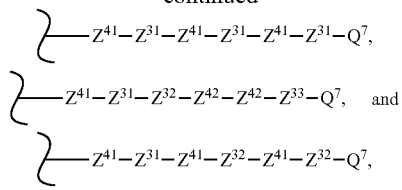

in which $Z^{41}$, $Z^{42}$, and $Z^{43}$ are different from one another, each representing a different aryl group and in which $Z^{31}$, $Z^{32}$, and $Z^{33}$ are different from one another and selected from formulae 24A, 24B, 24C, 24D, 25, 26, 27, 28, 29, and 30. In certain embodiments, each q is the same and is an integer greater than zero, each p is the same and is an integer greater than zero, each $Z^3$ is the same, and each $Z^4$ is the same. In certain embodiments each q is the same and is an integer greater than zero, and each p is one. In certain embodiments, each q is the same or different and is one, two, or three; and each p is the same or different and is one, two, or three. In certain embodiments, each q is the same and is one, two, or three; and each p is the same and is one, two, or three. In certain embodiments, each q is the same and is one, two, or three; each p is the same and is one, two, or three; each $Z^3$ is the same; and each $Z^4$ is the same.

Examples of compounds having formula 23 in which $Z^1$ has one of the following formulae 24C, 24D, 25, 26, 27, 28, 29, or 30 and in which $Q^5$ and $Q^6$ are chosen such that at least one of $Q^5$ and $Q^6$ is an aryl group having formula 34 include those having the formulae set forth below:

In certain embodiments, the aforementioned compounds have formula 23 in which $Z^1$ has one of the following formulae 24C, 24D, 25, 26, 27, 28, 29, or 30; in which one of $Q^5$ and $Q^6$ is an aryl group having formula 34; in which the other of $Q^5$ and $Q^6$ is an electron donating group or an electron accepting group; in which, when the other of $Q^5$ and $Q^6$ is an electron donating group, $Q^7$ is an electron accepting group; and in which, when the other of $Q^5$ and $Q^6$ is an electron accepting group, $Q^7$ is an electron donating group. In one illustrative example, $Q^6$ is an aryl group having formula 34; one of $Q^5$ and $Q^7$ is an electron donating group; and the other of $Q^5$ and $Q^7$ is an electron accepting group. In another illustrative example, $Q^5$ is an aryl group having formula 34; one of $Q^6$ and $Q^7$ is an electron donating group; and the other of $Q^6$ and $Q^7$ is an electron accepting group.

In certain embodiments, the aforementioned compounds have formula 23 in which $Z^1$ has one of the following formulae 24C, 24D, 25, 26, 27, 28, 29, or 30; in which one of $Q^5$ and $Q^6$ is an aryl group having formula 34; and in which the other of $Q^5$ and $Q^6$ is an aryl group having the formula:

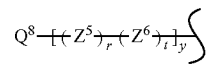

wherein each $Z^5$ is independently selected from formulae 24A, 24B, 24C, 24D, 25, 26, 27, 28, 29, and 30; wherein each $Z^6$ is the same or different and is an aryl group; wherein one

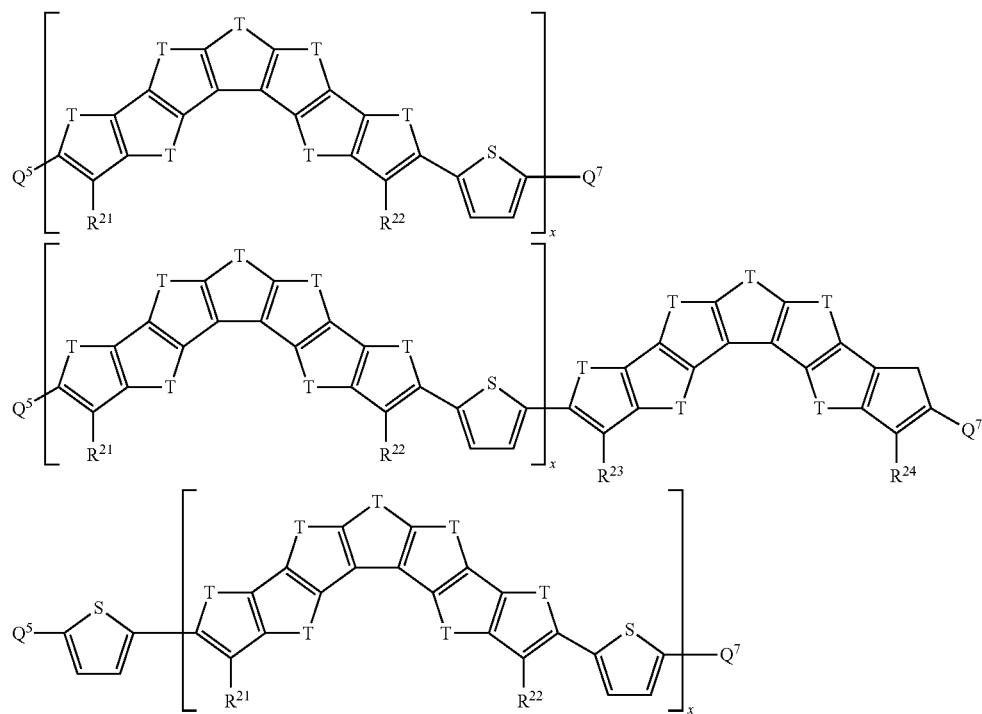

in which $R^{21}$, $R^{22}$, $R^{23}$, and $R^{24}$ are the same or different and each is independently selected from the moieties recited above for $R^1$ and $R^2$ (i.e., hydrogen, an alkyl group, or an aryl group); in which each T is independently selected from S and $SO_2$; and in which x is an integer greater than zero.

of $Q^7$ and $Q^8$ is an electron donating group or an electron accepting group; wherein, when $Q^7$ is an electron donating group, $Q^8$ is an electron accepting group; wherein, when $Q^7$ is an electron accepting group, $Q^8$ is an electron donating group; and wherein each r is the same or different and is zero or an integer greater than zero and each t is the same or different and is zero or an integer greater than zero, provided that at least one r or at least one t is not zero; and y is greater than or equal to one.

Compounds of the present invention having formula 23 wherein $Z^1$ has one of the formulae 24A, 24B, 24C, 24D, 25, 26, 27, 28, 29, or 30 can be prepared by any suitable method.

Figure 4:
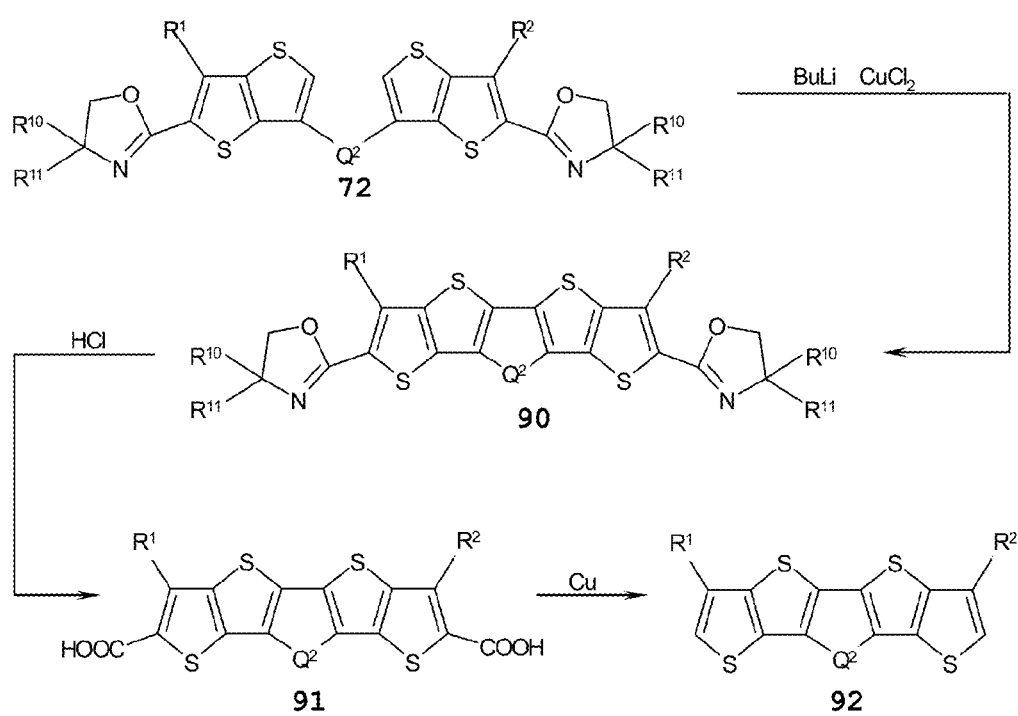
FIG. 4 is a synthetic scheme that can be used to prepare certain compounds of the present invention.

For example, compounds of formula 23 in which $Z^1$ has formula 24B wherein m is 2 or in which $Z^1$ had formula 24C can be prepared from compounds of the present invention having formula 14 in which $Q^2$ has formula 18, 22A, 22B, 22C, 22D, or 22E. Illustratively, compound 72 (e.g., prepared in accordance with the procedures described in FIG. 2A when $Q^2$ is S or in accordance with the procedures described above when $Q^2$ is —Se—, —Te—, —B($R^3$)—, —P($R^3$)—, or —Si($R^3$)($R^4$)—) can be treated with an alkyl lithium (e.g., butyl lithium) and a copper halide (e.g., $CuCl_2$) or iron salt (e.g., iron acetate) to produce compound 90, as shown in FIG. 4.

Compounds of formula 23 in which $Z^1$ has formula 24A in which n is 3 can be prepared from compounds having formula 16 or 17 in which $Q^2$ has formula 18. Illustratively, compound 78 (e.g., prepared in accordance with the procedures described in FIG. 2C) can be treated with an alkyl lithium (e.g., butyl lithium) and a copper halide (e.g., $CuCl_2$) or iron salt (e.g., iron acetate) to produce a compound in which $Z^1$ has formula 24A in which n is 3.

Compounds of formula 23 in which $Z^1$ has formula 24B wherein m is 3 or in which $Z^1$ had formula 24D can be prepared from compounds having formula 15 in which $Q^2$ has formula 18, 22A, 22B, 22C, 22D, or 22E. Illustratively, compound 74 (e.g., prepared in accordance with the procedures described in FIG. 2B when $Q^2$ is S or in accordance with the procedures described above when $Q^2$ is —Se—, —Te—, —B($R^3$)—, —P($R^3$)—, or —Si($R^3$)($R^4$)—) can be treated with an alkyl lithium (e.g., butyl lithium) and a copper halide (e.g., $CuCl_2$) or iron salt (e.g., iron acetate) to produce a compound of formula 23 in which $Z^1$ has formula 24B in which n is 3.

Compounds of formula 23 in which $Z^1$ has formula 24B in which m is 3 can alternatively be prepared from compounds having formula 14 in which $Q^2$ has formula 19 using an alkyl lithium (e.g., butyl lithium) and a copper halide (e.g., $CuCl_2$) or iron salt (e.g., iron acetate).

The aforementioned treatment with alkyl lithium (e.g., butyl lithium) and copper halide (e.g., $CuCl_2$) or iron salt (e.g., iron acetate) can also be used to prepare: (i) compounds of formula 23 in which $Z^1$ has formula 24B in which m is 4 from compounds having formula 15 in which $Q^2$ has formula 19; (ii) compounds of formula 23 in which $Z^1$ has formula 24A in which n is 4 from compounds having formula 14 in which $Q^2$ has formula 21B; (iii) compounds of formula 23 in which $Z^1$ has formula 24A in which n is 5 from compounds having formula 15 in which $Q^2$ has formula 21B; (iv) compounds of formula 23 in which $Z^1$ has formula 25 from compounds having formula 14 in which $Q^2$ has formula 20; (v) compounds of formula 23 in which $Z^1$ has formula 26 from compounds having formula 16 or 17 in which $Q^2$ has formula 20; (vi) compounds of formula 23 in which $Z^1$ has formula 27 from compounds having formula 15 in which $Q^2$ has formula 20; (vii) compounds of formula 23 in which $Z^1$ has formula 28 from compounds having formula 14 in which $Q^2$ has formula 21A; (viii) compounds of formula 23 in which $Z^1$ has formula 29 from compounds having formula 16 or 17 in which $Q^2$ has formula 21A; and (ix) compounds of formula 23 in which $Z^1$ has formula 30 from compounds having formula 15 in which $Q^2$ has formula 21A.

In all of the reactions discussed above, the starting materials (compounds having formula 14, 15, 16, or 17) can have terminal thiophene rings bearing an oxazoline moiety in the alpha position (i.e., compounds having formula 14, 15, 16, or 17 in which $Q^3$ and $Q^4$ are an oxazoline moieties). In such cases, the treatment with alkyl lithium (e.g., butyl lithium) and copper halide (e.g., $CuCl_2$) will generally not affect the oxazoline moiety, and, thus, compounds of formula 23 will have terminal thiophene rings bearing an oxazoline moiety in the alpha position.

As one skilled in the art will recognize, the oxazoline moiety can be readily converted (e.g., subsequent to treatment with alkyl lithium and copper halide) to the carboxylic acid (for example, by treatment with aqueous HCl), and the carboxylic acid can be converted to esters, amides, and other carboxylic acid derivatives using conventional procedures.

The aforementioned free carboxylic acids or carboxylic acid derivatives can then be converted to hydrogen, an alkyl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, a halide, etc. using conventional procedures.

For example, compounds of formula 23 having terminal thiophene rings bearing an oxazoline moiety in the alpha position can be converted to compounds of formula 23 having terminal thiophene rings bearing a carboxylic acid in the alpha position by treatment with aqueous HCl; and the carboxylic acid group can then be removed by conventional procedures, for example, by treatment with copper. A typical reaction sequence is illustrated in FIG. 4, in which a compound having thiophene rings bearing an oxazoline moiety in the alpha position (compound 90) is converted to a compound having thiophene rings bearing a carboxylic acid in the alpha position (compound 91) and then to a compound having thiophene rings having unsubstituted alpha positions (compound 92).

As further illustration, compounds of formula 23 having terminal thiophene rings bearing hydrogen in the alpha position can be converted to compounds of formula 23 having terminal thiophene rings bearing a halogen in the alpha position by treatment with a halogenating agent, such as N-bromosuccinimide. Compounds of formula 23 having terminal thiophene rings bearing a halogen in the alpha position can be readily converted to compounds of formula 23 having terminal thiophene rings bearing an aryl group in the alpha position by reaction with an aryl trialkyltin, such as an aryl trialkyltin having the formula $(R^{25})_3$Sn—Ar, wherein Ar comprises an aryl group and $R^{25}$ is an alkyl group. The coupling reaction can be performed in the presence of a catalyst, for example, a palladium catalyst, such as a Pd(0) catalyst, examples of which include $Pd(PPh_3)_4$.

As still further illustration, compounds of formula 23 having one terminal thiophene ring bearing hydrogen in the alpha position can be converted to compounds having formula 23 in which $Q^6$ has formula 31 (e.g., compounds having 32) using iron(III) compounds, such as $FeCl_3$ or $Fe(acac)_3$. Alternatively, such compounds (e.g., compounds having 32) can be prepared from compounds of formula 23 having one terminal thiophene ring bearing a halogen (e.g., Br) in the alpha position using organomagnesium mediated chemistries.

As yet further illustration, compounds of formula 23 having both terminal thiophene rings bearing hydrogen in the alpha positions can be converted to conjugated oligomers or polymers (e.g., having formula 23 in which $Q^6$ has formula 34 in which q is zero) using iron(III) compounds, such as $FeCl_3$ or $Fe(acac)_3$. Alternatively, such conjugated oligomers or polymers (e.g., having formula 23 in which $Q^6$ has formula 34 in which q is zero) can be prepared from compounds of formula 23 having both terminal thiophene rings bearing halogen (e.g., Br) in the alpha positions using organomagnesium mediated chemistries.

Figure 5:
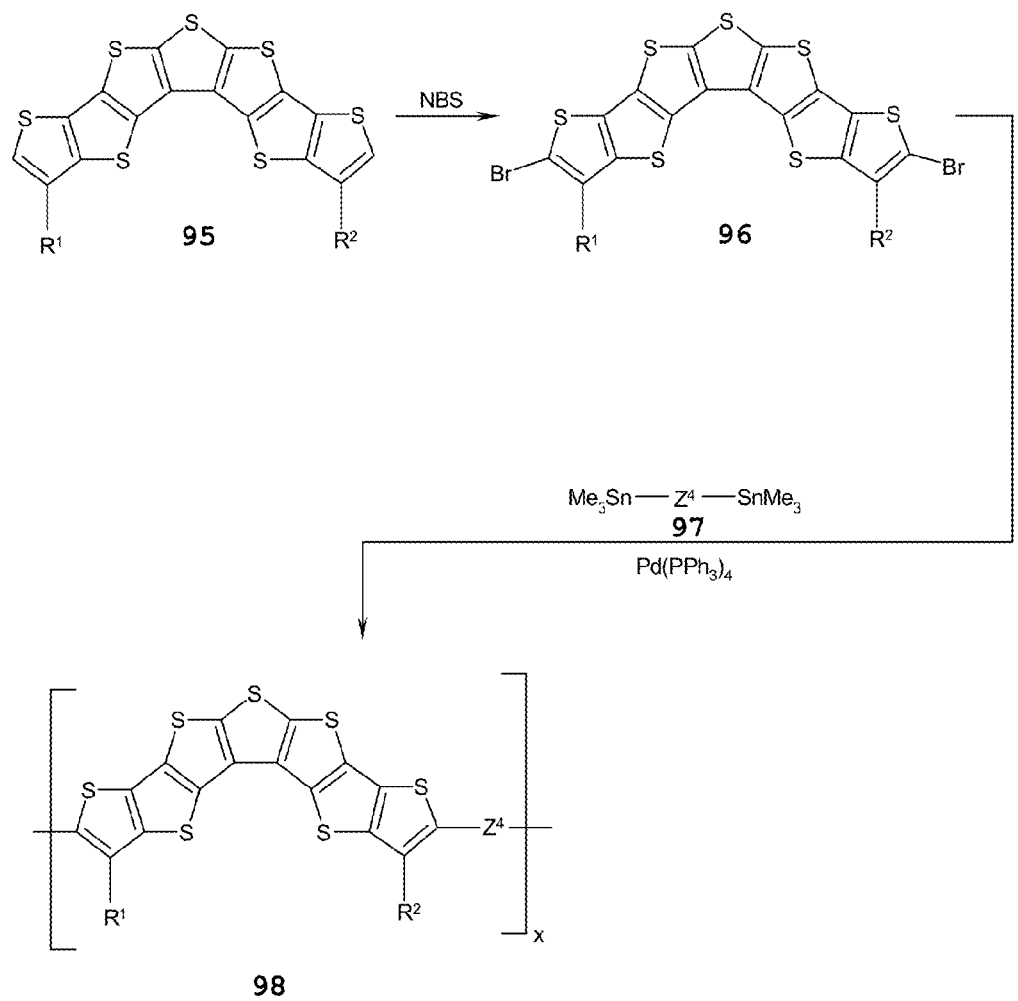
FIG. 5 is a synthetic scheme that can be used to prepare certain compounds of the present invention.

Similar chemistries can be used to prepare conjugated oligomers or polymers (e.g., having formula 23 in which $Q^6$ has formula 34 in which q is not zero). Illustratively, compounds of formula 23 having both terminal thiophene rings bearing a halogen in the alpha positions can be readily converted to compounds of formula 23 in which $Q^6$ has formula 34 wherein q is not zero by reaction with an aryl bis(trialkyltin), such as an aryl bis(trialkyltin) having the formula $(R^{25})_3Sn—Z^4—Sn(R^{25})_3$, wherein $Z^4$ comprises an aryl group and $R^{25}$ is an alkyl group, for example, by performing the coupling reaction in the presence of a catalyst (e.g., a palladium catalyst, such as a Pd(0) catalyst, examples of which include $Pd(PPh_3)_4$. FIG. 5 illustrates one embodiment of this method. Briefly, referring to FIG. 5, a compound of formula 23 having both terminal thiophene rings bearing halogen in the alpha positions (i.e., compound 96) (which can be prepared from a compound of formula 23 having both terminal thiophene rings bearing hydrogen in the alpha positions (i.e., compound 95), e.g., by treatment with N-bromosuccinimide) is coupled with distannyl aromatic compound 97 (e.g., a 2,5'-distannyl-trimethyl-bithiophene) in the presence of $Pd(PPh_3)_4$ to produce compound 98. Examples of suitable $Z^4$ moieties for use in distannyl aromatic compound 97 and compound 98 include those set forth above in the discussion regarding formula 34.

Using the methodologies described above, one skilled in the art can prepare oligomers, polymers, copolymers (e.g., block copolymers, condensation copolymers, etc.), and other compounds having formula 23 in which $Q^6$ has formula 34. In certain embodiments, such oligomers, polymers, copolymers, and other compounds having formula 23 in which $Q^6$ has formula 34 possess enhanced packing ability and thermal stability. In certain embodiments, they display liquid crystalline phases over certain temperature ranges, and the liquid crystalline properties can be tuned, for example, by choice of the groups $R^1$ and $R^2$ (e.g., by changing the length of $R^1$ and $R^2$ alkyl groups). In certain embodiments, such oligomers, polymers, copolymers, and other compounds having formula 23 in which $Q^6$ has formula 34 display no or substantially no liquid crystalline phases. In certain embodiments, they are amorphous; and in certain other embodiments, they are crystalline. Irrespective of whether the aforementioned oligomers, polymers, copolymers, and other compounds having formula 23 in which $Q^6$ has formula 34 are amorphous, crystalline, liquid crystalline, etc., in certain embodiments, they can have good solubility in organic solvents, such as, for example, tetrahydrofuran, toluene, chlorobenzene, and the like, for example, a degree of solubility in one or more of these or other solvents that permits the casting of thin films using techniques known in the art.

While the above discussion of oligomers, polymers, copolymers (e.g., block copolymers, condensation copolymers, etc.), and other compounds having formula 23 has focused on those in which $Z^1$ is bonded into the oligomer, polymer, and copolymer via the alpha positions(s) of the terminal thiophene(s) in $Z^1$ (i.e., the alpha positions(s) of the terminal thiophene(s) in 24A, 24B, 24C, 24D, 25, 26, 27, 28, 29, or 30), it will be appreciated that compounds of the present invention having formula 23 are meant to include oligomers, polymers, copolymers (e.g., block copolymers, condensation copolymers, etc.) in which $Z^1$ is bonded into the oligomer, polymer, and copolymer via other groups, such as where $Z^1$ is bonded into the oligomer, polymer, and copolymer via one or more of $Z^1$'s $R^1$ and $R^2$ groups.

Moreover, while the above discussion of oligomers, polymers, copolymers (e.g., block copolymers, condensation copolymers, etc.), and other compounds having formula 23 has focused on those in which $Z^1$ is bonded into the oligomer, polymer, and copolymer via an aryl moiety (e.g., as in the case where $Q^6$ is an aryl group), it will be appreciated that compounds of the present invention having formula 23 are meant to include oligomers, polymers, copolymers (e.g., block copolymers, condensation copolymers, etc.) in which $Z^1$ is bonded into the oligomer, polymer, and copolymer via other moieties. For example, $Z^1$ can be bonded into the oligomer, polymer, and copolymer via other moieties commonly used in conjugated polymers, such as vinylene moieties. As further illustration, $Z^1$ can be incorporated into the main chain of an oligomer, polymer, or copolymer, for example, as in the case where $Z^1$ is incorporated into the main chain of conjugated or unconjugated polymer (such as a polyester, a polyurethane, a polyether, a polyamide, a polycarbonate, or a polyketone) or as in the case where $Z^1$ is incorporated into a side chain of a polymer (such as a polyacrylate, a polymethacrylate, or a poly(vinyl ether)). It will be appreciated that $Z^1$ can be incorporated into such conjugated or unconjugated polymers via the alpha positions(s) of the terminal thiophene(s) in $Z^1$ or via other groups, such as via one or more of $Z^1$'s $R^1$ and $R^2$ groups; and it will be appreciated that compounds of the present invention having formula 23 are meant to encompass such conjugated or unconjugated polymers (e.g., conjugated or unconjugated polymers which include one or more $Z^1$ moieties having formulae 24C, 24D, 25, 26, 27, 28, 29, or 30).

Compounds of the present invention having formula 23 are also meant to include monomeric compounds in which at least one of $Q^5$ and $Q^6$ is or contains a reactive group that permits and/or facilitates the monomeric compound to be incorporated into a polymer (e.g., as in the case where at least one of $Q^5$ and $Q^6$ is an acyl chloride; an alcohol; an acrylate; an amine; a vinyl ether; an alkyl group substituted with an acyl chloride, an alcohol, an acrylate, an amine, a vinyl ether, etc.; an aryl group substituted with an acyl chloride, an alcohol, an acrylate, an amine, a vinyl ether, etc.; and the like). Compounds of the present invention having formula 23 are also meant to include monomeric compounds in which at least one of $R^1$ and $R^2$ contains a reactive group that permits and/or facilitates the monomeric compound to be incorporated into a polymer (e.g., as in the case where at least one of $R^1$ and $R^2$ is an alkyl or aryl group substituted with or otherwise containing an acyl chloride, an alcohol, an acrylate, an amine, a vinyl ether, etc.).

As noted above, in compounds of the present invention having formula 23, T can be S or $SO_2$. The oxidized compounds of the present invention having formula 23 (i.e., those in which at least some of the T's are $SO_2$) can be prepared by oxidation, for example, with a peracid, such as 3-chloroperoxybenzoic acid (MCPBA). Oxidation is generally selective at the central-most rings of the polycyclic fused thiophene ring systems; however, it is contemplated that any of the sulfur atoms in the fused thiophenes can be oxidized. It is also contemplated that oxidation can be carried out at any suitable stage. Illustratively, oxidation can be carried out on compounds of formula 23 that have terminal thiophene rings bearing a free carboxylic acid in the alpha position, that have terminal thiophene rings bearing hydrogen in the alpha position, that have terminal thiophene rings bearing a halogen in the alpha position, or that have been incorporated into an oligomer or polymer.

Compounds of formula 23 can be used in a variety of applications, for example, in a wide variety of devices, such as electronic, optoelectronic, and nonlinear optical devices.

Examples of such devices include field effect transistors (FETs), thin-film transistors (TFTs), organic light-emitting diodes (OLEDs), polymer light-emitting diodes (PLEDs), electro-optic (EO) devices, RFID tags, electroluminescent devices (such as those found in flat panel displays), photovoltaic devices, chemical or biological sensors, laser frequency converters, optical interferometric waveguide gates, wideband electrooptical guided wave analog-to-digital converters, optical parametric devices, and devices described in U.S. Pat. Nos. 4,767,169, 4,775,215, 4,795,664, 4,810,338, 4,936,645, 5,006,285, 5,044,725, 5,106,211, 5,133,037, 5,170,461, 5,187,234, 5,196,509, 5,247,042, 5,326,661, and 6,584,266, which are hereby incorporated by reference. In certain embodiments, monomers, oligomers, polymers, and other compounds of formula 23 can be used as conductive materials, as optical waveguides, as two photon mixing materials, as organic semiconductors, and/or as non-linear optical (NLO) materials.

By way of further illustration donor-acceptor chromophore compounds of formula 23 can be used in optical waveguides for laser modulation and deflection, information control in optical circuitry, as well as in numerous other waveguide applications. The optical waveguides can be used in a variety of optical devices, such as laser frequency converters, optical interferometric waveguide gates, wideband electrooptical guided wave analog-to-digital converters, optical parametric devices, and those described in, for example, U.S. Pat. Nos. 5,044,725, 4,795,664, 5,247,042, 5,196,509, 4,810,338, 4,936,645, 4,767,169, 4,775,215, 5,326,661, 5,187,234, 5,170,461, 5,133,037, 5,106,211, and 5,006,285, which are hereby incorporated by reference. Examples of such optical waveguides include those which comprise a thin film medium having one of the following formulae 101, 102, and 103:

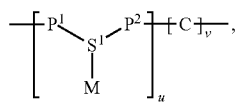

101

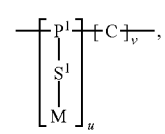

102

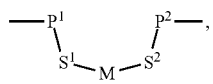

103 in which $P^1$ and $P^2$ are polymer main chain units, which can be the same mer unit or different mer unit; C is a comonomer unit where u is an integer greater than zero and v is 0 or an integer greater than zero; $S^1$ and $S^2$ are pendant spacer groups having a linear chain length of between about 2-12 atoms; and M is a donor-acceptor chromophore compound of formula 23.

By way of illustration, M can be a compound of formula 23 in which $Q^5$ is an electron donor and in which $Q^6$ is an electron acceptor and in which M is bonded to spacer S via the beta substituent(s) on the terminal thiophene ring(s), e.g., via $R^1$ and/or $R^2$.

Pendant spacer groups, $S^1$ and $S^2$, that can be employed include those described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, which are hereby incorporated by reference.

Polymers and copolymers, $P^1$, $P^2$, and C, that can be employed include those that are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, which are hereby incorporated by reference. In certain embodiments, the polymers are homopolymers. In certain embodiments, the polymers are copolymers. Examples of polymers and copolymers include acrylate, vinyl carboxylate, substituted arylvinyl, vinyl halide, vinyl carboxylate, alkene, alkadiene, arylvinyl, methacrylate, vinyl chloride, vinyl acetate, vinyl ether, ethylene, propylene, isobutylene, 1-butene, isoprene, styrene, and the like. In certain embodiments, the polymers comprise an external field-induced orientation and alignment of pendant side chains. In certain embodiments, the polymer main chain is a structural type such as polyvinyl, polyoxyalkylene, polysiloxane, polycondensation, and the like. The polymer can be applied to a supporting substrate by conventional methods, such as spin coating, dip coating, spraying, Langmuir-Blodgett deposition, and the like. The thin film optical waveguide medium after fabrication can be subjected to an external field to orient and align uniaxially the polymer side chains. In one method, the polymer medium is heated close to or above the polymer glass transition temperature $T_g$, then an external field (e.g., a DC electric field) is applied to the medium of mobile chromophore molecules to induce uniaxial molecular alignment of the chromophore polymer side chains or guests in a guest-host system parallel to the applied field, and the medium is cooled while maintaining the external field effect.

As noted above, certain aspects of the present invention (e.g., those discussed above in relation to FIGS. 3A and 3B) involve the use of di(trialkyltin sulfide) thiophenes and di(trialkyltin sulfide) thienothiophenes. These compounds, to which the present invention also relates, are described in greater detail below.

The present invention also relates to a compound having one of the following formulae 37, 38, 39, or 40:

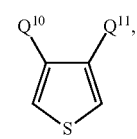

37

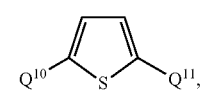

38

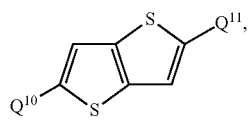

39

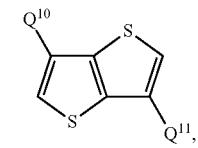

40 wherein $Q^{10}$ and $Q^{11}$ are the same or different and have the formula:

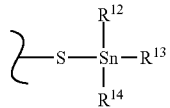

wherein $R^{12}$, $R^{13}$, and $R^{14}$ are independently selected from alkyl and aryl. In certain embodiments, $Q^{10}$ and $Q^{11}$ are the same. In certain embodiments, $Q^{10}$ and $Q^{11}$ are the same, and $R^{12}$, $R^{13}$, and $R^{14}$ are the same. In certain embodiments, $R^{12}$, $R^{13}$, and $R^{14}$ are alkyl, such as where $R^{12}$, $R^{13}$, and $R^{14}$ are the same or different C2 to C6 alkyl, where $R^{12}$, $R^{13}$, and $R^{14}$ are the same or different C3 or C4 alkyl, and/or where $R^{12}$, $R^{13}$, and $R^{14}$ are butyl. In certain embodiments, the compound has either formula 37 or formula 38. In certain embodiments, the compound has either formula 39 or formula 40.

Compounds having formulae 37, 38, 39, or 40 can be prepared by any suitable method, for example, from the corresponding dihalo thiophenes and dihalo thienothiophenes by treatment with an alkyl lithium compound (e.g., butyl lithium), followed by reaction with sulfur, and then with a trialkyl tin halide (e.g., tributyl tin chloride). Illustratively, compounds having formula 37, 38, 39, and 40 can be prepared following the procedures described in FIGS. 6A, 6B, 6C, and 6D, respectively. For example, in FIG. 6A, dihalo thiophene 110 is first reacted with an alkyl lithium compound (e.g., butyl lithium), followed by reaction with sulfur and then with a trialkyl tin halide (e.g., tributyl tin chloride) to produce di(trialkyltin sulfide) thiophene 111; in FIG. 6B, dihalo thiophene 112 is first reacted with an alkyl lithium compound (e.g., butyl lithium), followed by reaction with sulfur and then with a trialkyl tin halide (e.g., tributyl tin chloride) to produce di(trialkyltin sulfide) thiophene 113; in FIG. 6C, dihalo thienothiophene 114 is first reacted with an alkyl lithium compound (e.g., butyl lithium), followed by reaction with sulfur and then with a trialkyl tin halide (e.g., tributyl tin chloride) to produce di(trialkyltin sulfide) thienothiophene 115; and in FIG. 6D, dihalo thienothiophene 116 is first reacted with an alkyl lithium compound (e.g., butyl lithium), followed by reaction with sulfur and then with a trialkyl tin halide (e.g., tributyl tin chloride) to produce di(trialkyltin sulfide) thienothiophene 117.

The aforementioned compounds of the present invention having formulae 37, 38, 39, or 40 can be used, for example, in the preparation of compounds of the present invention having formulae 14, 15, 16, or 17 (e.g., using the procedures discussed above in relation to FIGS. 3A and 3B).

The present invention also relates to a compound having one of the following formulae 41, 42, 43, 44, 45, or 46:

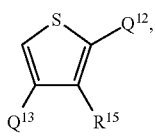

41

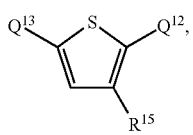

42

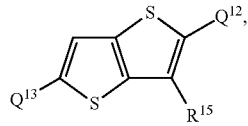

43

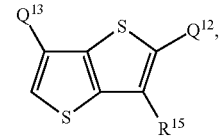

44

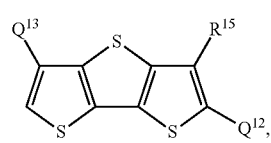

45

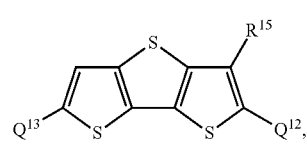

46 wherein $R^{15}$ is selected from hydrogen, alkyl, and aryl; wherein $Q^{12}$ is selected from hydrogen, a carboxylic acid, a carboxylic acid derivative, an alkyl group, an aryl group, an aldehyde group, an aldehyde derivative, a ketone group, a hydroxyl group, an unsubstituted thiol group, a substituted thiol group, an alkoxy group, an acrylate group, an amino group, a vinyl group, a vinyl ether group, or a halide; and wherein $Q^{13}$ has the formula:

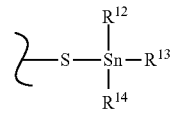

wherein $R^{12}$, $R^{13}$, and $R^{14}$ are independently selected from alkyl and aryl.

As noted above, $R^{15}$ is a hydrogen, an alkyl group, or an aryl group. Illustratively, $R^{15}$ can be a variety of substituted or unsubstituted alkyl groups. For example, $R^{15}$ can be an unsubstituted alkyl group, such as a straight-chain alkyl group (e.g. methyl, ethyl, propyl, butyl, pentyl, hexyl, heptyl, octyl, nonyl, decyl, undecyl, dodecyl or hexadecyl), a branched alkyl group (e.g. sec-butyl, neo-pentyl, 4-methyl-pentyl), or a substituted or unsubstituted cycloalkyl group (e.g. cyclopentyl, cyclohexyl). In certain embodiments, $R^{15}$ is an alkyl group at least four carbons in size. In certain embodiments, $R^{15}$ is a substituted alkyl group at least four carbons in size. In certain embodiments, $R^{15}$ is a substituted alkyl group at least four carbons in size in which substitution of the alkyl group is separated from the fused thiophene ring system by at least two carbons. In certain embodiments, $R^{15}$ is an alkyl group substituted with an aryl group, cycloalkyl group, aralkyl group, an alkenyl group, an alkynyl group, an amino group, an ester, an aldehyde, a hydroxyl group, an alkoxy group, a thiol group, a thioalkyl group, a halide, an acyl halide, an acrylate, or a vinyl ether. Examples of substituted alkyl groups include, but are not limited to, 6-hydroxyhexyl and 3-phenylbutyl. As with the selection of $R^1$ in the context of compounds having the formula 11 or 12, selection of $R^{15}$ here can depend on the end use of the compound. The methods described herein permit the synthesis of fused thiophene moieties having a wide variety of $R^{15}$ substituents, and any functionality that might be present on a substituted alkyl or aryl $R^{15}$ group can be protected, for example, in order to survive subsequent reaction steps.

In certain embodiments, $Q^{12}$ is a hydrogen. In certain embodiments, $Q^{12}$ is an aldehyde group. In certain embodiments, $Q^{12}$ is an aldehyde derivative. Examples of aldehyde derivatives include aldehyde protecting groups, such as acetals (e.g., cyclic acetals). In certain embodiments, $Q^{12}$ is a carboxylic acid. In certain embodiments, $Q^{12}$ is a carboxylic acid derivative. Examples of carboxylic acid derivatives include carboxylic acid esters (e.g., substituted alkyl esters, unsubstituted alkyl esters, substituted C1-C6 alkyl esters, unsubstituted C1-C6 alkyl esters, substituted aryl esters, unsubstituted aryl esters, etc.); carboxylic acid amides (e.g., unsubstituted amides, monosubstituted amides, disubstituted amides, etc.); acyl halides (e.g., acyl chlorides, etc.); carboxyl protecting groups; and the like. In certain embodiments, $Q^{12}$ is a carboxyl protecting group. Examples of carboxyl protecting groups include esters, thioesters, and oxazolines. As particular examples, there can be mentioned linear alkyl esters (e.g., linear C1-C8 alkyl esters, such as methyl esters, for example, where $Q^5$, $Q^6$, or both $Q^5$ and $Q^6$ are $—COOCH_3$); tertiary alkyl esters (e.g., tertiary C4-C8 alkyl esters, such as t-butyl esters, for example, where $Q^5$, $Q^6$, or both $Q^5$ and $Q^6$ are $—COOC(CH_3)_3$); aralkyl esters (e.g., (C6-C10)aryl-substituted-(C1-C4)alkyl esters, such as benzyl esters, for example, where $Q^5$, $Q^6$, or both $Q^5$ and $Q^6$ are $—COOCH_2(C_6H_5)$); and tertiary alkyl thioesters (e.g., tertiary C4-C8 alkyl thioesters, such as t-butyl thioesters, for example, where $Q^5$, $Q^6$, or both $Q^5$ and $Q^6$ are $—C(O)SC(CH_3)_3$). As noted above, $Q^5$, $Q^6$, or both $Q^5$ and $Q^6$ can be an oxazoline moiety, such as a 1,3-oxazolin-2-yl moiety, for example, as in the case $Q^5$, $Q^6$, or both $Q^5$ and $Q^6$ have the formula:

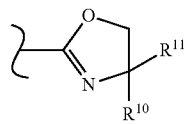

in which $R^{10}$ and $R^{11}$ are the same or different and are selected from hydrogen, alkyl (e.g., a substituted or unsubstituted C1-C8 alkyl), and aryl (e.g., a substituted or unsubstituted phenyl) or $R^{10}$ and $R^{11}$, together with the carbon atom to which they are bound, form a ring (e.g., a 4- to 8-membered (such as a 5-membered, 6-membered, etc.) homocyclic or heterocyclic ring). Illustratively, $R^{10}$ and $R^{11}$ can be the same or different lower alkyl, such as in the case where $R^{10}$ and $R^{11}$ are the same or different and are selected from a C1-C6 alkyl. In certain embodiments, $R^{10}$ and $R^{11}$ are the same lower alkyl, for example as in the case where each of $R^{10}$ and $R^{11}$ is a methyl group, an ethyl group, a n-propyl group, and i-propyl group, etc.

In certain embodiments, $R^{12}$, $R^{13}$, and $R^{14}$ are the same. In certain embodiments, $R^{12}$, $R^{13}$, and $R^{14}$ are alkyl, such as where $R^{12}$, $R^{13}$, and $R^{14}$ are the same or different C2 to C6 alkyl, where $R^{12}$, $R^{13}$, and $R^{14}$ are the same or different C3 or C4 alkyl, and/or where $R^{12}$, $R^{13}$, and $R^{14}$ are butyl. In certain embodiments, the compound has formula 41. In certain embodiments, the compound has formula 42. In certain embodiments, the compound has formula 42. In certain embodiments, the compound has formula 43. In certain embodiments, the compound has formula 44. In certain embodiments, the compound has formula 45. In certain embodiments, the compound has formula 46.

Compounds having formulae 41, 42, 43, 44, 45, or 46 can be prepared by any suitable method, for example, from the corresponding halo thiophenes, halo thienothiophenes, and halo dithienothiophenes by treatment with an alkyl lithium compound (e.g., butyl lithium), followed by reaction with sulfur, and then with a trialkyl tin halide (e.g., tributyl tin chloride). Illustratively, compounds having formulae 43 and 45 can be prepared from compounds having formulae 11 and 12 using the reaction described above in relation to FIG. 6A.

The aforementioned compounds of the present invention having formulae 41, 42, 43, 44, 45, or 46 can be used, for example, in the preparation of compounds of the present invention or other thiophene-containing compounds as would be apparent to those skilled in the art, for example, from the discussion presented above and from the examples which follow.

Certain embodiments of the compounds and methods described hereinabove may overcome or otherwise address some or all of the problems that have been encountered in the synthesis of fused thiophenes, for example, as described below.

Figure 7:
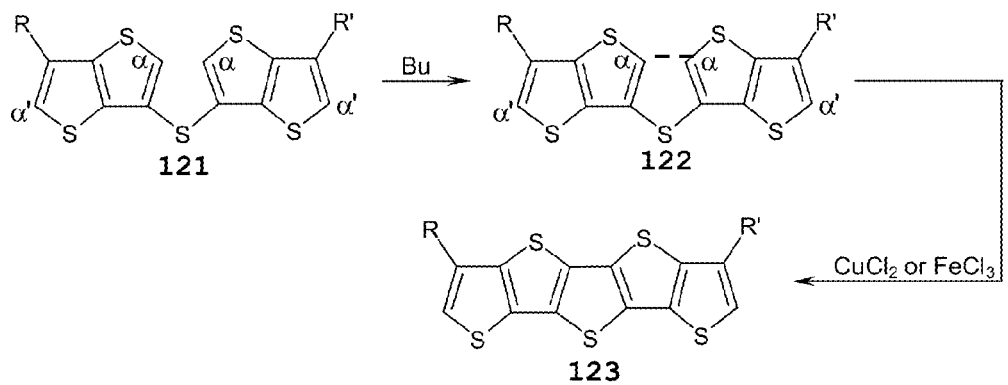
FIG. 7 is a synthetic scheme showing a prior art method for preparing fused thiophenes.

Most of the previously reported synthetic methods are limited to unsubstituted fused thiophenes or alkyl substituted fused thiophene compounds with a small number of fused rings (e.g. two or three rings) (Mazaki et al., *Tetrahedron Lett.*, 25:3315-3318 (1989); Zhang et al., *J. Am. Chem. Soc.*, 127:10502-10503 (2005); Xiao et al., *J. Am. Chem. Soc.*, 27:13281-13286 (2005); Sato et al., *J. Chem. Soc. Perkin Trans. 2*, 765-770 (1992); Okamoto et al., *Org. Lett.*, 23:5301-5304 (2005); Toshihiro et al., *Chem. Eur. J.*, 13:548-556 (2007); Zhang et al., *J. Macromolecules*, 37:6306-6315 (2004); Armitage et al., *Science & Engineering*, 51:771 (2006); and Meyers et al., *J. Org. Chem.*, 39(18): 2787-2793 (1974), which are hereby incorporated by reference). A commonly used synthetic method for making larger fused thiophene compounds is illustrated in FIG. 7. It involves the use of butyl lithium as a strong base to generate a double anion (122) from a sulfide-coupled bis(thienothiophene) (121). These anions (122) are then oxidized by introducing appropriate oxidative reagents such as $CuCl_2$ or $FeCl_3$ to facilitate the ring closure and formation of the fused thiophene compound (123). Typical yields are 10% to 30%. However, there are some problems with this synthetic procedure. For example, sulfide-coupled bis(thienothiophene) (121) has four α-hydrogen atoms (labeled α and α'), and all of these hydrogens are believed to have approximately the same reactivity toward strong base. Therefore, when butyl lithium is introduced to the reaction, all four hydrogens can be removed to form anions. This mixture of anions in different positions may lead to a low yield of desired intermediate 122, which may result a low yield of compound 123. Moreover, the sulfide-coupled bis(thienothiophene) (121) usually has poor solubility at low temperature in solvents appropriate for the butyl lithium reaction, and this can further affect the overall yield. It is believed that certain embodiments of the synthetic routes and intermediates described herein may improve the yield of β-alkyl substituted fused thiophene compounds (such as 123) or other fused thiophenes.

In particular, certain embodiments of the synthetic routes and intermediates described herein may be better (e.g., in terms of yield) for synthesizing larger fused ring thiophenes, e.g., larger than 4 (although it is to be understood that the usefulness of such synthetic routes and intermediates is not limited to fused ring thiophenes of these sizes). For example, in certain embodiments, the use of a carboxy protecting group (e.g., an oxazoline carboxy protecting group) in the synthetic process prior to carrying out the ring coupling and ring closure steps may act to (i) enhance the reactants solubility and/or (ii) to block anion formation at unwanted reactive sites. In certain embodiments, the overall yield of fused thiophene is improved despite the process having more steps than conventional procedures (e.g., five steps vs. three for conventional procedures). Additionally or alternatively, the use of certain embodiments of the synthetic routes and intermediates described herein can overcome or otherwise address the solubility limitations of conventional methods. These solubility limitations typically limit the conventional methods' utility to the preparation of thiophenes with 5 fused rings or fewer in poor yields. In contrast, using certain embodiments of the synthetic routes and intermediates described herein can permit the facile preparation of fused thiophenes having a greater number constituent fused thiophene rings.

Figure 8:
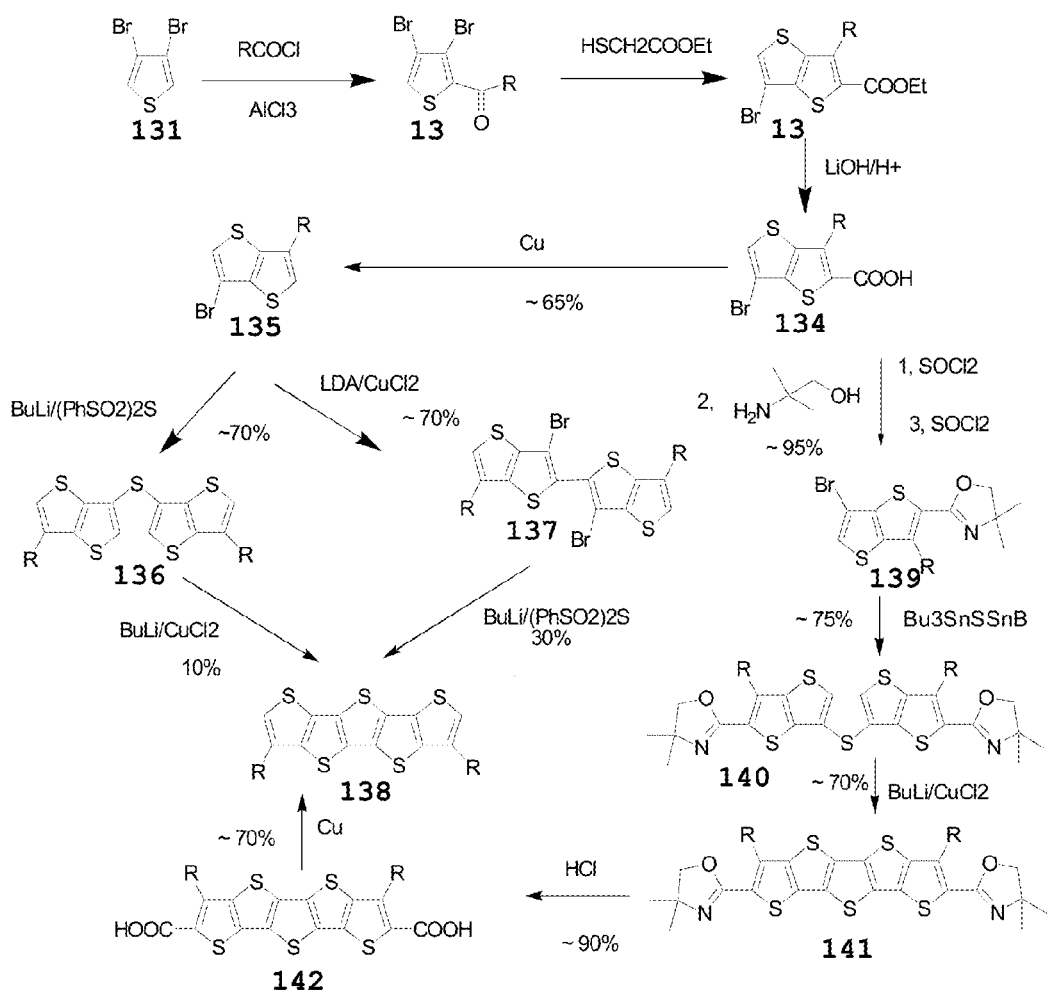
FIGS. 8 and 9 are a synthetic scheme comparing prior art methods and compounds for preparing fused thiophenes to certain methods and compounds of the present invention.
Figure 9:
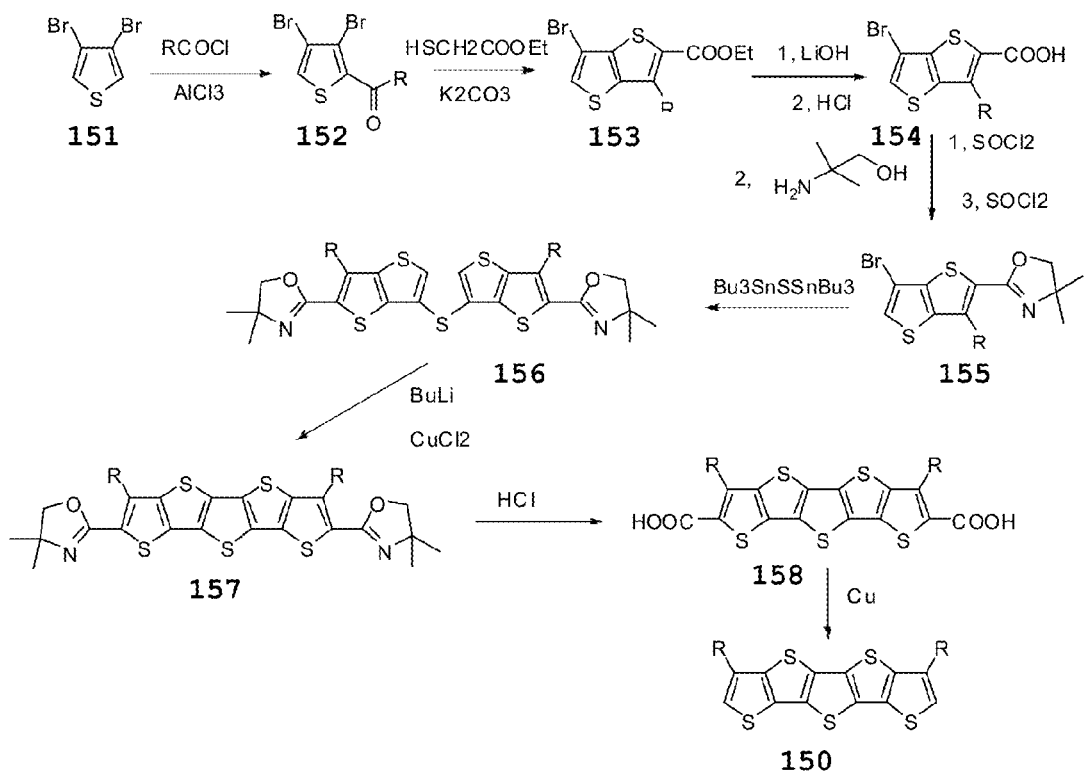

FIG. 8 sets forth a comparison of prior art methods (described in PCT Patent Application Publication No. WO 2006/031893 and He et al., *J. Org. Chem.*, 72(2):444-451 (2007), which are hereby incorporated by reference) and an embodiment of the synthetic routes and intermediates of the present invention. Referring to FIG. 8, one of the key intermediates in the prior art methods is compound 135 that is generated via decarboxylation of compound 134. Although a good yield can be obtained from this reaction, the poor solubility of compound 136 and/or lack of selectivity between reaction sites on compound 137 give a low yield of compound 138. In this regard, note that the 30% yield set forth in FIG. 8 for the 137 to 138 conversion is for situations where 137 is soluble (i.e., in cases where 138 has five or fewer rings). In contrast, the embodiment of the synthetic routes and intermediates of the present invention set forth in FIG. 8 (134 to 139 to 140 to 141 to 142 to 138) can have one or more of the following advantages: (i) the overall yield of the 134 to 139 to 140 to 141 to 142 to 138 five-step sequence of this embodiment of the present invention can be greater than 30%, while the overall yield of the 134 to 135 to 136 to 138 and 134 to 135 to 137 to 138 three-step sequences of the prior method were only on the order of 5% and 15%, respectively; (ii) this embodiment of the present invention can overcome or otherwise address the solubility limitations of the prior method, which can limit the prior method's utility to the preparation of thiophenes with 5 fused rings or fewer; (iii) this embodiment of the present invention makes possible the facile preparation of fused thiophenes containing a greater number of fused rings; (iv) because of the poor yields of the 136 to 138 and 137 to 138 transformations in the prior method, the purity of the fused ring thiophene obtained as the final product (138) can be poor, whereas, in this embodiment of the present invention, purification of intermediates can be easier (e.g., because of cleaner and/or higher yield reactions) and the purity of the final product (138) can be significantly higher; (v) even though this embodiment of the present invention involves five steps in going from 134 to 138 vs. three steps in the two prior approaches (134 to 135 to 136 to 138 and 134 to 135 to 137 to 138, the advantages gained in the final purification and/or yield of 138 can more than offset the additional number of steps involved (e.g., because the workup involved in each of the five steps is fairly easy, generally involving only simple washing procedures (and, in some cases, not requiring any workup prior to use in the next step); because the overall yield for the five-step sequence can be more than twice that of the three-step sequences; etc.). As is the case will all of the figures of the present application, the reactions set forth in FIG. 8 are meant to be illustrative only, and many other chemistries and strategies can be used to effect particular conversions. For example, in FIG. 8, the conversion of 139 to 140 is shown as being carried out using $Bu_3SnSSnBu_3$. However, this conversion can be effected using other chemistries and strategies. For example, 140 can be produced by treating 139 with butyl lithium (or another alkyl lithium) to form the corresponding beta anion and reacting the resulting beta anion with $(PhSO_2)_2$ S or another bis(arylsulfonyl)sulfide (e.g., using procedures analogous to those described in PCT Patent Application Publication No. WO 2006/031893 and He et al., *J. Org. Chem.*, 72(2):444-451 (2007), which are hereby incorporated by reference).

The present invention is further illustrated by the following non-limiting examples.

EXAMPLES

Example 1

FIG. 8 shows a synthetic scheme for the preparation of a five-membered fused thiophene 150 using compounds and procedures described hereinabove. Details regarding this synthetic scheme are set forth in the following Example 2-9.

Example 2

3,4-Dibromothienyl-2-tetradecyl-ketone (152) was prepared using the following procedure. To a mixture of 3,4-dibromothiophene (151) (36.30 g, 0.15 mol) and $AlCl_3$ (46.20 g, 0.345 mol) in $CH_2Cl_2$ (400 mL) at 0° C., myristoyl chloride (38.90 g, 0.16 mol) was added dropwise under a nitrogen stream. This was stirred for 0.5 hours until no starting materials could be detected by GC/MS. The mixture was then poured into HCl (500 mL, 6M), and the organic was extracted with hexanes (2×300 mL). The combined organic solution was washed with brine (2×150 mL) and water (150 mL). After drying over anhydrous $MgSO_4$, the solvent was evaporated. A low melting point solid was collected and was pure enough to be used without further purification (68.0 g, 100%). Mp: 50-52° C., GC-MS 453[M+], $^1$H NMR (300 MHz, $CD_2Cl_2$) δ 7.64 (s, 1H), 3.03 (t, 2H), 1.71 (t, 2H), 1.27 (m, 22H), 0.88 (t, 3H).

Example 3

3-Tridecyl-6-bromo-ethylthieno[3,2-b]thiophene-2-carboxylate (153) was prepared using the following procedure. Compound 152 (68.0 g, 0.15 mol) was mixed with $K_2CO_3$ (82.80 g, 0.60 mol) and DMF (350 mL) in a three neck flask equipped with a condenser and addition funnel. To this mixture, ethyl mercaptoacetate (16.42 mL, 0.15 mol) was added dropwise at 60-70° C. A catalytic amount of 18-crown-6 (20 mg) was used as catalyst. The mixture was heated at 60-70° C. overnight until no starting materials were detected by GC/MS. The mixture then was poured into water (600 mL) and extracted by ethylacetate (2×250 ml). Organic washed by brine (3×400 ml) and dried by $MgSO_4$. After evaporating the solvent, the brownish crude target was obtained and found to be pure enough for the next reaction (71.0 g, 100%). GC/MS 473[M+].

Example 4

3-Tridecyl-6-bromo-thieno[3,2-b]thiophene-2-carboxylic acid (154) was prepared using the following procedure. Compound 153 (71.0 g, 0.15 mol) was dissolved into a mixture of THF (400 mL), methanol (50 mL), and LiOH (72 mL, 10% solution). This mixture was refluxed overnight and poured into concentrated hydrochloric acid (300 mL). The acid mixture was then diluted to 1000 mL with water. Solid was filtrated and washed with water (3×500 mL). The light yellow solid was washed with methanol (300 mL) and dried under vacuum overnight (46.40 g. 69.5%). Mp: 88-90° C. $^1$H NMR (300 MHz, $CD_2Cl_2$) δ 7.55 (s, 1H), 3.17 (t, 2H), 1.75 (t, 2H), 1.26 (m, 20H), 0.87 (t, 3H).

Example 5

2-(3-Tridecyl-6-bromo-thieno[3,2-b]thienyl)-4,4-dimethyl-2-oxazoline (155) was prepared using the following procedure. 3-Tridecyl-6-bromo-thieno[3,2-b]thiophene-2-carboxylic acid (154) (46.12 g, 0.10 mol) was added to 100 ml of thionyl chloride, and the mixture was stirred at room temperature for 24 hours. The excess thionyl chloride was distilled, and the remaining dark oil was distilled by rotating evaporate to yield 48.46 g (100%) of the acid chloride. The 48.46 g (0.10 mol) of acid chloride was dissolved in 100 ml of methylene chloride and added in a dropwise manner to a magnetically stirred solution of 18.51 g (0.2 mol) of 2-amino-2-methyl-1-propanol in 100 ml of methylene chloride at 0° C. The mixture was stirred at 25° C. for 2 hours. After evaporating the solvent, the organic was extracted with ethylacetate (2×200 mL). The combined organic solution was washed with brine (2×150 mL) and water (150 mL). After drying over anhydrous $MgSO_4$, the solvent was evaporated to give oil crude product 47.37 g (91.80%) of N-(2,2-dimethyl-3hydroxypropyl)-3-tridecyl-6-bromo-thieno[3,2-b]thienylamide. To cyclize the amide, thionyl chloride (43.67 g, 0.37 mol) was added dropwise with stirring to 43.37 g (0.092 mol) of the amide. When the vigorous reaction had subsided, the yellow solution was poured into 150 ml water. Organics were extracted with ethylacetate (3×100 mL). The combined organic extracts were washed with brine (2×100 mL) and water (100 mL). After drying over anhydrous $MgSO_4$, the target was purified by silica column chromatography, eluting with 20% ethylacetate/hexane (43.00 g, 93.85%). Mp: 37-39° C. $^1$H NMR (300 MHz, $CD_2Cl_2$) δ 7.39 (s, 1H), 4.08 (s, 2H), 3.16 (t, 2H), 1.26-1.70 (m, 28H), 0.86 (t, 3H).

Example 6

Bis(2-(4,4-dimethyl-2-oxazolyl)-3-tridecyl-thieno[3,2-b]thienyl)sulfide (156) was prepared using the following procedure. Compound (155) (24.25 g, 0.0487 mol) was added to a solution of bis(tri-n-butyltin)sulfide (15.67 g, 0.0256 mmol) and $Pd(PPh_3)_4$ (2.25 g, $1.95\times10^{-3}$ mol) in toluene (40 mL) under nitrogen. The mixture was placed in a pressure vessel and heated at 125° C. for 60 hours. After filtration, the organic solution was diluted with hexane (300 mL) and solid was precipitated. The solid was re-crystallized from acetone to give 156 (11.5 g, 76.7%). Mp: 67-69° C. $^1$H NMR (300 MHz, $CD_2Cl_2$) δ 7.64 (s, 2H), 4.08 (s, 4H), 3.07 (t, 4H), 1.25-1.66 (m, 56H), 0.86 (t, 6H).

Example 7

Bis(2-(4,4-dimethyl-2-oxazolyl)-3-tridecyl)-heptathienoacene (157) was prepared using the following procedure. To a solution of compound 156 (9.0 g, 10.4 mmol) in THF (100 mL), n-butyllithium (10.4 mL, 2.50M in hexane, 25.90 mmol) was added dropwise at 0° C. under argon. This mixture was stirred at 0° C. for 30 minutes and then warmed to room temperature for 2 hours before cooling it to 0° C. again. Copper (II) chloride (3.50 g) powder was added to the reaction solution. This mixture was stirred overnight and then poured into water (200 mL). The water solution was heated to boiling, and the solid was filtered. The solid was placed in water (200 mL) and heated again. After filtration, the solid was washed with hot acetone (100 mL) and hot ethanol (100 mL). The yellow solid was boiled in toluene (400 mL) and was hot filtered. The solution was cooled to room temperature to give compound 157 as a yellow solid (6.00 g, 66.6%). Mp: 116-118° C. $^1$H NMR (300 MHz, $CD_2Cl_2$) δ 4.34 (s, 4H), 3.10 (t, 4H), 1.26-1.75 (m, 56H), 0.87 (t, 6H).

Example 8

3,6-ditrideyl-heptathienoacene-2,7-dicarboxylate acid (158) was prepared using the following procedure. Compound 157 (6.00 g, 6.93 mmol) was mixed with HCl (4N, 10 mL) and THF (50 mL) and heated to reflux for 30 mins. This mixture was acidified with concentrated HCl (30 mL). The solid that formed was filtered and washed with water several times, then washed by acetone (3×100 ml). The solid was dried under vacuum and was not further purified to give (4.75 g, 90.2%). The compound was not soluble enough for NMR. Mp: 242-244° C.

Example 9

3,7-Ditridecyl-heptathienoacene (150) was prepared using the following procedure. Compound 158 (3.17 g, 4.2 mmol) was mixed with copper powder (0.40 g) in quinoline (80 mL). The mixture was heated to 240-250° C. in a Woods-metal bath until no gas bubbles were detected. The mixture was cooled to room temperature, and hot hexane (400 mL) was added. This mixture was then repeatedly washed with HCl (2N, 4×50 mL). The hexane then was partially evaporated. The target compound was collected by filtration and re-crystallized from hexane to afford 150 (1.50 g, 53.5%). Mp: 66-67° C. $^1$H NMR (300 MHz, $C_6D_6$) δ 7.02 (s, 2H), 2.76 (t, 4H), 1.26-1.81 (m, 44H), 0.87 (t, 6H).

Example 10

Figure 6A:
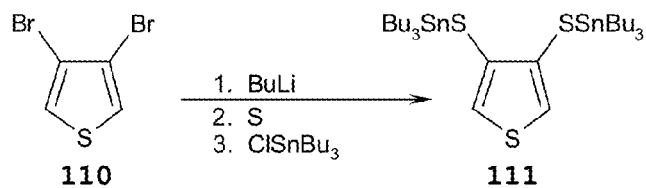
FIGS. 6A-6D are synthetic schemes that can be used to prepare certain compounds of the present invention.

Synthesis of 3,4-bis(tributylstannyl)thiophene (111) according to the scheme of FIG. 6A To 6.80 g (28.11 mmol) of 3,4-dibromothiophene (110) in 15 mL of dry $Et_2O$ at −78° C. under $N_2$ protection, 23.6 mL of 2.5 M n-BuLi (59.02 mmol) in hexane was added dropwise. The resulting solution was stirred at −78° C. for 20 minutes. 1.80 g (56.13 mmol) of sulfur flowers was then added into this solution to form a cloudy solution. After this solution was stirred at −78° C. for 2 hours, 16.8 mL of $Bu_3SnCl$ (62.30 mmol) was added to it. A clear solution formed was then refluxed for 12 hours. 150 mL of $CH_2Cl_2$ and 100 mL of water were added into this reaction mixture after it was warmed to room temperature. After this mixture was stirred for 10 minutes, the organic layer was collected and was washed with saturated $NaHCO_3$ solution (60 mL) and brine (50 mL). The organic layer was then collected and dried over anhydrous $Na_2SO_4$. Solvents were removed from it to yield an oily product that was kept at 150° C. in Kugelrohr vacuum for 8 hours to yield compound 111 as an oily residue (4.90 g, 24%). $^1$H NMR (300 MHz, $CD_2Cl_2$): δ 7.08 (s, 2H), 1.62-0.83 (m, 54H).

Example 11

Figure 6B:
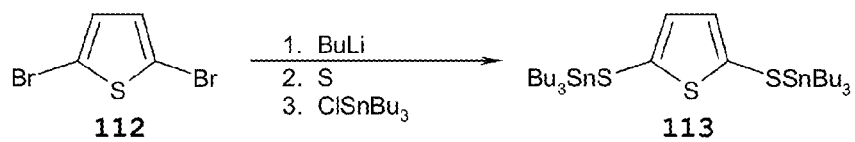
Figure 6C:
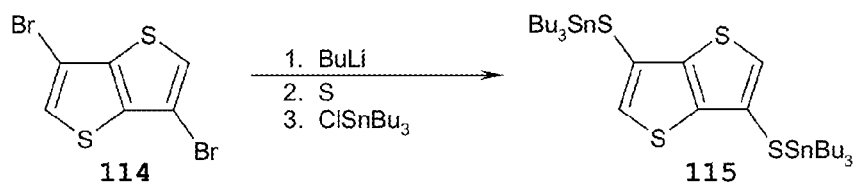
Figure 6D:
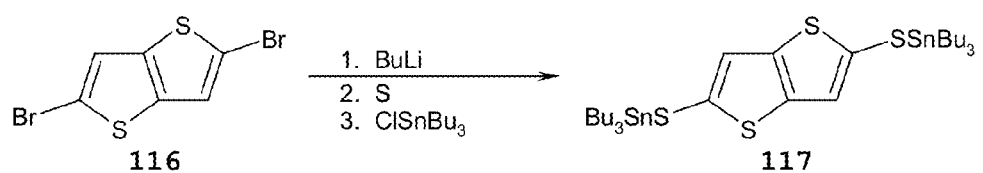

Synthesis of 2,5-bis(tributylstannyl)thiophene (113) according to the scheme of FIG. 6B To 3.22 g (13.31 mmol) of 2,5-dibromothiophene (112) in 90 mL of dry $Et_2O$ at −78° C. under $N_2$ protection, 10.6 mL of 2.5 M n-BuLi (26.5 mmol) in hexane was added dropwise.

The resulting solution was stirred at −78° C. for 20 minutes. 0.86 g (26.82 mmol) of sulfur flowers was then added into this solution to form a cloudy solution. After this solution was stirred at −78° C. for 2 hours, 7.36 mL of Bu₃SnCl (27.29 mmol) was added to it. A clear solution formed was then refluxed for 12 hours. 150 mL of hexane and 100 mL of water were added into this reaction mixture after it was warmed to room temperature. After this mixture was stirred for 10 minutes, the organic layer was collected and was washed with saturated NaHCO₃ solution (60 mL) and brine (50 mL). The organic layer was collected and dried over anhydrous Na₂SO₄. Solvents were removed from it to yield an oily product of compound 113 that was kept at 150° C. in Kugelrohr vacuum for 8 hours to yield compound 5 as an oily residue (4.78 g, 49%). ¹H NMR (300 MHz, CD₂Cl₂): δ 7.33 (s, 2H), 1.62-0.83 (m, 54H).

Example 12

Figure 10:
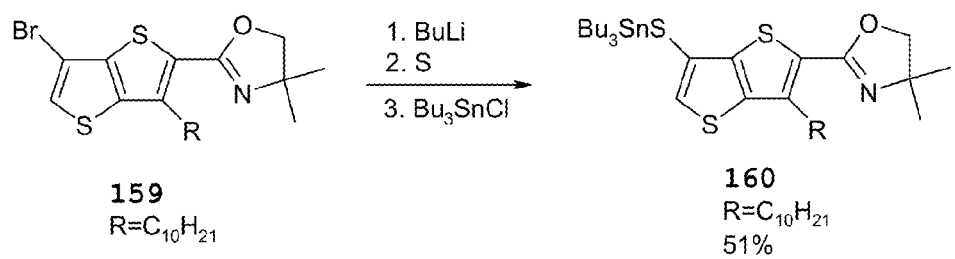
FIGS. 10 and 11 are synthetic schemes that can be used to prepare certain compounds of the present invention.

Synthesis of 2-(6-(tributyltin)sulfanyl-3-decyl-thieno[3,2-b]thiophen-2-yl)-4,4-dimethyl-4,5-dihydro-oxazole (160) according the scheme of FIG. 10

To 940 mg (2.1 mmol) of vacuum-dried 2-(6-bromosulfanyl-3-decyl-thieno[3,2-b]thiophen-2-yl)-4,4-dimethyl-4,5-dihydro-oxazole (159) in 10 mL of dry Et₂O at −78° C. under N₂ protection, 0.83 mL of 2.5 M n-BuLi (2.06 mmol) in hexane was added dropwise. The resulting solution was stirred at −78° C. for 20 minutes. 66 mg (2.06 mmol) of sulfur flowers was then added into this solution to form a cloudy solution. After this solution was stirred at 0° C. for 40 minutes, 0.61 mL (2.26 mmol) of Bu₃SnCl was added into it. A clear solution formed was then refluxed for 6 hours. 60 mL of CH₂Cl₂ and 50 mL of water were added into this reaction mixture after it was warmed to room temperature. After this mixture was stirred for 10 minutes, the organic solution was collected and was washed with saturated NH₄Cl solution (2×20 mL) and water (50 mL). The organic layer was collected and dried over anhydrous Na₂SO₄. Solvents were removed from it and the residue was crystallized from ethanol and then cooled in the refrigerator to give 0.91 grams of compound 2 as a wet solid of compound 160 (yield 51%). ¹H NMR (300 MHz, CD₂Cl₂): δ 7.19 (s, 1H), 4.06 (s, 2H), 3.10 (t, 2H), 1.77-1.07 (m, 55H); HRMS (ESI) m/z calcd for [C₄₆H₆₀S₇+1] 700.27. found 700.26.

Example 13

Figure 11:
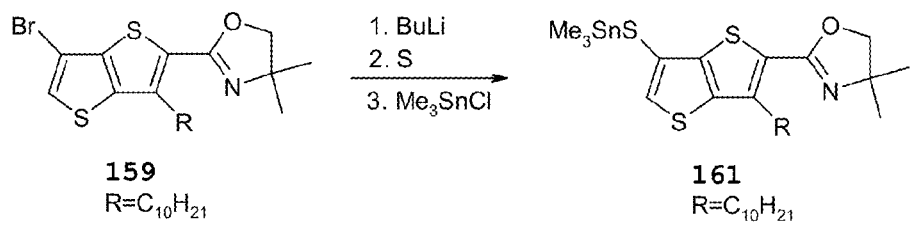

Synthesis of 2-(6-(trimethyltin)sulfanyl-3-decyl-thieno[3,2-b]thiophen-2-yl)-4,4-dimethyl-4,5-dihydro-oxazole (161) according the scheme of FIG. 11

Under N₂ protection, 1.29 mL of 2.5 M n-BuLi (3.23 mmol) in hexane was added dropwise to a solution of 2-(6-bromosulfanyl-3-decyl-thieno[3,2-b]thiophen-2-yl)-4,4-dimethyl-4,5-dihydro-oxazole (159) (1.34 g, 2.94 mmol) in 10 mL of dry Et₂O at −78° C. After this resulting solution was stirred at −78° C. for one hour, 94 mg (2.93 mmol) of sulfur flowers was added into this solution to form a cloudy solution. After this solution was stirred at 0° C. for 40 minutes, a solution of 1 M Me₃SnCl (3.23 mL, 3.23 mmol) in THF was added. A clear solution formed was refluxed for 6 hours. 60 mL of CH₂Cl₂ and 50 mL of water were added into this reaction mixture after it was warmed to room temperature. After this mixture was stirred for 10 minutes, the organic layer was collected and was washed with saturated NaHCO₃ solution (2×20 mL) and brine (50 mL). The organic layer was collected and dried over anhydrous Na₂SO₄. Solvents were removed from it to form a wet solid that was crystallized from methanol and then cooled in the refrigerator to give 1.27 grams of compound 161 as a solid. HRMS (ESI) m/z calcd for [C₄₆H₆₀S₇+1] 574.12. found 574.11.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention, as defined in the claims which follow.

The invention claimed is:
1. A compound having one of the following formulae 41, 42, 43, 44, 45, or 46:

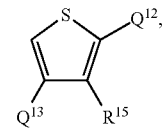

41

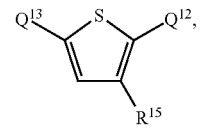

42

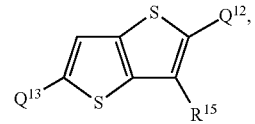

43

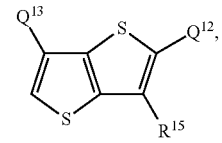

44

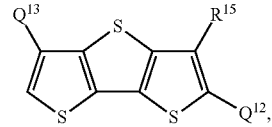

45

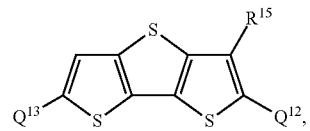

46 wherein $R^{15}$ is selected from hydrogen, alkyl, and aryl; wherein $Q^{12}$ is selected from hydrogen, a carboxylic acid, a carboxylic acid derivative, an alkyl group, an aryl group, an aldehyde group, an aldehyde derivative, a ketone group, a hydroxyl group, an unsubstituted thiol-group, a substituted thiol group, an alkoxy group, an acrylate group, an amino group, a vinyl group, a vinyl ether group, or a halide; and wherein $Q^{13}$ has the formula:

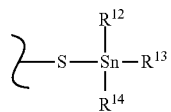

wherein $R^{12}$, $R^{13}$, and $R^{14}$ are independently selected from alkyl and aryl.

2. A compound according to claim 1, wherein $Q^{12}$ is a carboxyl protecting group or an aldehyde protecting group.

3. A compound according to claim 1, wherein $Q^{12}$ is an oxazoline moiety.

4. A compound according to claim 1, wherein $Q^{12}$ has the formula:

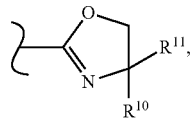

wherein $R^{10}$ and $R^{11}$ are the same or different and are selected from hydrogen, alkyl, and aryl or $R^{10}$ and $R^{11}$, together with the carbon atom to which they are bound, form a ring.

5. A compound according to claim 4, wherein $R^{10}$ and $R^{11}$ are the same or different and are lower alkyl.

6. A compound according to claim 4, wherein $R^{10}$ is a methyl group and $R^{11}$ is a methyl group.

7. A compound according to claim 1, wherein $R^{12}$, $R^{13}$, and $R^{14}$ are alkyl.

8. A compound according to claim 1, wherein $R^{12}$, $R^{13}$, and $R^{14}$ are C2 to C6 alkyl.

9. A compound according to claim 1, wherein $R^{12}$, $R^{13}$, and $R^{14}$ are C3 or C4 alkyl.

10. A compound according to claim 1 wherein $R^{12}$, $R^{13}$, and $R^{14}$ are butyl.

* * * * *